United States Patent [19]
Godlewski et al.

[11] Patent Number: 6,066,740
[45] Date of Patent: *May 23, 2000

[54] PROCESS FOR MAKING 2-AMINO-2-IMIDAZOLINE, GUANIDINE AND 2-AMINO-3,4,5,6-TETRAHYDROPYRIMIDINE DERIVATIVES

[75] Inventors: Michael Selden Godlewski, South Plymouth, N.Y.; Sean Rees Klopfenstein, Loveland, Ohio; Sreenivasa Reddy Mundla, Norwick, N.Y.; William Lee Seibel, Hamilton, Ohio; Randy Stuart Muth, Poolville, N.Y.

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/977,907

[22] Filed: Nov. 25, 1997

[51] Int. Cl.[7] ............... C07D 223/14; C07D 223/16; C07D 223/18; C07D 225/24
[52] U.S. Cl. ............... 548/347.1; 548/348.1; 548/349.1; 548/350.1; 548/351.1; 548/352.1; 544/330; 564/230; 564/231
[58] Field of Search ............... 564/230, 231; 548/347.1, 348.1, 349.1, 350.1, 351.1, 352.1; 544/242, 330

[56] References Cited

U.S. PATENT DOCUMENTS

| | | |
|---|---|---|
| 3,950,333 | 4/1976 | Durant et al. . |
| 4,762,932 | 8/1988 | Yellin et al. ............... 548/198 |
| 5,130,441 | 7/1992 | Gluchowski . |
| 5,332,745 | 7/1994 | Carter et al. ............... 514/275 |

FOREIGN PATENT DOCUMENTS

| | | |
|---|---|---|
| 1112648 | 12/1979 | Canada . |
| 16 70 807 | 3/1971 | Germany . |
| WO 97/08145 | 3/1997 | WIPO . |

OTHER PUBLICATIONS

H. Kohn, et al., "Syntheses and Pharmacological Activity of Substituted Imidazolidinethiones and Thioimidazolines," Journal of Medicinal Chemistry, vol. 20, No. 1, 1977, pp. 158–160.

M. Yokoyama, et al., "The Reaction of Imidazolidine–2–thione with Carbon Disulphide," J.C.S. Perkin I, pp. 2499–2503, 1981.

M. Yokoyama, et al., "Ring Cleavage of Cyclic Thioureas; A Synthesis of N–(Alkylthio–carbonyl)– '–(alkylthio–thiocarbonyl)–alkanediamines and N,N'–Bis[alkylthio–thiocarbonyl]–alkanediamines,"Communications, Nov. 1981, pp. 908–910.

P. B. M. W. M. Timmermans, et al., "Quantitative Relationships between α–Adrenergic Activity and Binding Affinity of α–Adrenoceptor Agonists and Antagonists," J. Med. Chem., 1984, 27, pp. 495–503.

H. Kohn, "Model Studies on the Mechanism of Biotin Dependent Carboxylations," Journal of the American Chemical Society, 98:12, Jun. 9, 1976, pp. 3690–3694.

H. Kohn, et al., "Syntheses and Spectral Properties of Substituted Imidazolidones and Imidazolines,"J. Org. Chem., vol. 42, No. 6, 1977, pp. 941–948.

J. G. Roberts, "Some Disubstituted Derivatives of Imidazolidin–2–one," J. Amer. Chem. Soc., 76, 1836, 1954, pp. 176–178.

C. B. Chapleo, et al., "Heteroaromatic Analogues of the $α_2$–Adrenoreceptor Partial Agonist Clonidine,"J. Med. Chem. 1989, 32, pp. 1627–1630.

A. Kosasayama, et al., Cyclic Guanidines III. Synthesis of Hypoglycemic 2–Benzhydrylimino–1,3–diazacycloalkanes, Chemical & Pharmaceutical Bulletin, vol. 27, No. 4, 1979, pp. 831–840.

S. R. Aspinall, et al., "A Synthesis of 2–Alkylamino–4,5–dihydroimidazoles,"The Monomagnesium Derivatives of Dibromotoluenes, Feb., 1951, pp. 602–603.

Najer et al., "A New Synthesis of 2–Arylaminoimidazolines", Memoires presented to the Chemical Society, pp. 2114–2126, (1961).

Bergmann, J. et al., "Synthesis and Structure–Activity Relationship of Some New Blocking Agents With Possible Alpha–Adrenoreceptor Activity", Arch. Pharm. (Weinheim), Vol. 323, No. 7 pp. 387–391 (1990).

Chapleo, et al., "Heteroaromatic Analogues of $α_2$–Adrenoreceptor Partial Agonist Clonidine", American Chemical Society, 1627–1630, (1989).

Primary Examiner—Nathan M. Nutter
Attorney, Agent, or Firm—James C. Kellerman; Mary Pat McMahon

[57] ABSTRACT

The present invention provides a process for making 2-amino-2-imidazoline, guanidine, and 2-amino-3,4,5,6-tetrahydroyrimidine derivatives by preparing the corresponding activated 2-thio-substituted-2-derivative in a two-step, one-pot procedure and by further reacting yields this isolated derivative with the appropriate amine or its salts in the presence of a proton source. The present process allows for the preparation of 2-amino-2-imidazolines, quanidines, and 2-amino-3,4,5,6-tetrahydropyrimidines under reaction conditions that eliminate the need for lengthy, costly, or multiple low yielding steps, and highly toxic reactants. This process allows for improved yields and product purity and provides additional synthetic flexibility.

18 Claims, No Drawings

PROCESS FOR MAKING 2-AMINO-2-IMIDAZOLINE, GUANIDINE AND 2-AMINO-3,4,5,6-TETRAHYDROPYRIMIDINE DERIVATIVES

FIELD OF THE INVENTION

The present invention relates to chemical processes for making compounds useful in the treatment of various medical disorders, including respiratory disorders, ocular disorders, gastrointestinal disorders, nasal decongestion, hypertension, migraine, disorders associated with sympathetic nervous system activity, and substance abuse. In particular, the processes of this invention are useful for making 2-amino-2-imidazoline derivatives, guanidine derivatives, and 2-amino-3,4,5,6-tetrahydropyrimidine derivatives.

BACKGROUND OF THE INVENTION

The present invention relates to processes for making 2-amino-2-imidazoline derivatives, guanidine derivatives, and 2-amino-3,4,5,6-tetrahydropyrimidine derivatives (all herein collectively described as "2-amino-2-derivatives"). Such derivatives are useful for the treatment of many medical disorders including, for example, respiratory disorders, ocular disorders, gastrointestinal disorders, nasal decongestion, hypertension, migraine, disorders associated with sympathetic nervous system activity, and substance abuse. One of the most widely known of these derivatives is clonidine, an alpha-2-adrenoreceptor agonist and antihypertensive agent. Iopidine is also a known alpha-2-adrenoreceptor agonist useful in reducing intraocular pressure:

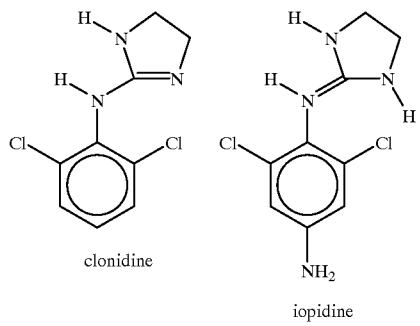

Clonidine, disclosed in U.S. Pat. No. 3,202,660 (1965) to Boehringer, Ing.; Iopidine, disclosed in U.S. Pat. No. 4,517,199 (1985) to Alcon; Timmermans, P. B. M. W. M., de Jonge, A., Thoolen, M. J. M. C., Wilffert, B., Batink, H., van Zwieten, P. A., "Quantitative Relationships between α-Adrenergic Activity and Binding Affinity of α-Adrenoceptor Agonists and Antagonists", Journal of Medicinal Chemistry Vol. 27 (1984) pp. 495–503; Physician's Desk Reference (50th ed., 1996).

Therapeutic indications of alpha-2-adrenoreceptor agonists have been discussed in the literature. Ruffolo, R. R., Nichols, A. J., Stadel, J. M., and Hieble, J. P., "Pharmacologic and Therapeutic Applications of Alpha-2-Adrenoceptor Subtypes", Annual Review of Pharmacology & Toxicology Vol. 32 (1993) pp. 243–279.

Further information regarding alpha adrenergic receptors, agonists and antagonists, in general, are disclosed in the following references: Timmermans, P. B. M. W. M., Chiu, A. T., and Thoolen, M. J. M. C., "12.1 α-Adrenergic Receptors", Comprehensive Medicinal Chemistry, Vol. 3, Membranes & Receptors, P. G. Sammes & J. B. Taylor, eds., Pergamon Press (1990), pp. 133–185; Timmermans, P. B. M. W. M., and van Zwieten, P. A., "α-Adrenoceptor Agonists and Antagonists", Drugs of the Future, Vol. 9, No. 1, (January, 1984), pp. 41–55; Megens, A. A. H. P., Leysen, J. E., Awouters, F. H. L., and Niemegeers, C. J. E., "Further Validation of in vivo and in vitro Pharmacological Procedures for Assessing the $\alpha_1$ and $\alpha_2$-Selectivity of Test Compounds: (2) α-Adrenoceptor Agonists", European Journal of Pharmacology, Vol. 129 (1986), pp. 57–64; Timmermans, P. B. M. W. M., de Jonge, A., Thoolen, M. J. M. C., Wilffert, B., Batink, H., van Zwieten, P. A., "Quantitative Relationships between α-Adrenergic Activity and Binding Affinity of α-Adrenoceptor Agonists and Antagonists", Journal of Medicinal Chemistry, Vol. 27 (1984) pp. 495–503; van Meel, J. C. A., de Jonge, A., Timmermans, P. B. M. W. M., and van Zwieten, P. A., "Selectivity of Some Alpha Adrenoceptor Agonists for Peripheral Alpha-1 and Alpha-2 Adrenoceptors in the Normotensive Rat", The Journal of Pharmacology and Experimental Therapeutics, Vol. 219, No. 3 (1981), pp. 760–767; Chapleo, C. B., et. al., "Effect of 1,4-Dioxanyl Substitution on the Adrenergic Activity of Some Standard α-Adrenoreceptor Agents", European Journal of Medicinal Chemistry, Vol. 24 (1989), pp. 619–622; Chapleo, C. B., et. al., "Heteroaromatic Analogues of the $\alpha_2$-Adrenoreceptor Partial Agonist Clonidine", Journal of Medicinal Chemistry, Vol. 32 (1989), pp. 1627–1630; Clare, K. A., Scrutton, M. C., and Thompson, N. T., "Effects of $\alpha_2$-Adrenoceptor Agonists and of Related Compounds on Aggregation of, and on Adenylate Cyclase Activity in, Human Platelets", British Journal of Pharmacology, Vol. 82 (1984), pp. 467–476; U.S. Pat. No. 3,890,319 issued to Danielewicz, Snarey, and Thomas, Jun. 17, 1975; U.S. Pat. No. 5,091,528 issued to Gluchowski, Feb. 25, 1992; U.S. Pat. No. 5,478,858 issued to Cupps and Bogdan, Dec. 26, 1995; and U.S. Pat. No. 5,541,210 issued to Cupps and Bogdan, Jul. 30, 1996.

In the art, 2-amino-2-derivatives have been synthesized according to many different methods. U.S. Pat. No. 4,398,028 issued to Neumann, Aug. 9, 1983; Chapleo, C., et. al., "Heteroaromatic Analogues of the $\alpha_2$-Adrenoreceptor Partial Agonist Clonidine", Journal of Medicinal Chemistry, Vol. 32 (1989) pp. 1627–1630; U.S. Pat. No. 5,130,441 issued to Gluchowski, Jul. 14, 1992; U.S. Pat. No. 5,478,858 issued to Cupps and Bogdan, Dec. 26, 1995.

For example, the synthesis of clonidine analogs involves the reaction of 2-thiomethyl-2-imidazoline with an aromatic primary amine in the presence of a large excess of pyridine. However, the literature cites very low yields in this reaction. See Chapleo, C., et. al., "Heteroaromatic Analogues of the $\alpha_2$-Adrenoreceptor Partial Agonist Clonidine", Journal of Medicinal Chemistry, Vol. 32 (1989) pp. 1627–1630.

Alternative syntheses of 2-amino-2-derivatives have been performed. However, of further disadvantage in these syntheses is the time-consuming, costly, multiple steps required by these syntheses, and/or the use of mercuric or other transition metal reagents which can result in the presence of toxic impurities. U.S. Pat. No. 4,398,028 issued to Neumann, Aug. 9, 1983; U.S. Pat. No. 5,478,858 issued to Cupps and Bogdan, Dec. 26, 1995.

Still further, other synthetic preparations of 2-amino-2-derivatives have been performed. U.S. Pat. No. 5,130,441 issued to Gluchowski, Jul. 14, 1992. Gluchowski found that yields in the formation of 2-amino-2-imidazolines could be improved over the Chapleo procedure by coupling an aromatic primary amine with an imidazoline sulfonic acid. However, yield improvements in Gluchowski were only moderate. Further, this synthesis required the low yielding preparation of an imidazoline sulfonic acid intermediate.

It is apparent from the art that higher yielding, more economical methods of preparing 2-amino-2-derivatives would be advantageous. It has been surprisingly discovered that the disadvantages of the literature syntheses of these compounds may be overcome by coupling a primary amine or its salts with an acylated 2-thio-substitued-2-imidazoline, -amidine, or -tetrahydropyrimidine intermediate in the presence of a proton source to give the desired 2-amino-2-derivative in one step. Yields in this reaction are significantly higher than those reported in Chapleo. The reaction is also more favorable than the Neumann and Cupps procedures because it overcomes lengthy syntheses and avoids the use of transition metal reagents.

Further, the present invention overcomes the deficiency of the Gluchowski synthesis. The present invention utilizes, not a sulfonic acid, but rather an acylated 2-thio-substitited-2-imidazoline, -amidine, or -tetrahydropyrimidine as the intermediate in the synthesis of 2-amino-2-derivatives. Generally, acylated, 2-thio-substituted-2-imidazolines are known. However, the known syntheses of acylated 2-thiomethyl-2-imidazolines provide low yields. Kohn, H., et. al., "Syntheses and Pharmacological Activity of Substituted Imidazolinethiones and Thioimidazolines", *Journal of Medicinal Chemistry,* Vol. 20 (1977) pp. 158–160; Kohn, H., et. al., "Syntheses and Spectral Properties of Substituted Imidazolidones and Imidazolines", *Journal of Organic Chemistry,* Vol. 42 (1977) pp. 941–948. It has been surprisingly discovered that acylated 2-thio-substituted-2-imidazolines, -amidines, and -tetrahydropyrimidines can be prepared in a two-step, one-pot procedure in high yields. This procedure renders the synthesis of acylated 2-thio-substituted-2-derivatives higher yielding, easier, and less time consuming than the procedure in the Kohn reference.

It has therefore now been discovered that 2-amino-2-imidazoline, guanidine, and 2-amino-3,4,5,6-tetrahydropyrimidine derivatives may be conveniently synthesized in high yields by preparing the corresponding acylated 2-thio-substituted-2-derivative in a two-step, one-pot procedure in high yields and by further reacting this isolated derivative with the appropriate amine or its salts in the presence of a proton source. The present process allows for the preparation of 2-amino-2-imidazolines, guanidines, and 2-amino-3,4,5,6-tetrahydropyrimidines under reaction conditions that eliminate the need for lengthy, costly, or multiple low yielding steps, and highly toxic reactants. This process allows for improved yields and product purity and provides additional synthetic flexibility for the preparation of these classes of molecules.

In particular, the preferred processes of the present invention provide a new methodology that is especially suited for the scale-up and manufacture of 2-amino-2-derivatives. The processes utilize commercially-available, low-cost starting materials. The acylated 2-thio-substituted-2-imidazoline, -amidine, or -tetrahydropyrimidine intermediate and the corresponding 2-amino-2-derivative can often be obtained by direct precipitation, thus avoiding the typical extraction and evaporation procedures which are encountered in the literature procedures.

SUMMARY OF THE INVENTION

The present invention provides a process for making 2-amino-2-imidazoline, guanidine, and 2-amino-3,4,5,6-tetrahydropyrimidine derivatives having a general structure:

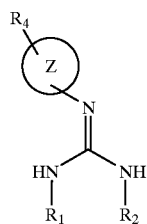

or the tautomers thereof, wherein:

(a) $R_1$ is methyl, ethyl, a methylene group connected to $R_2$ through a single bond such that $R_1$ and $R_2$ form a five-membered ring, or a methylene group connected to $R_2$ through another methylene group such that $R_1$ and $R_2$ form a six-membered ring;

(b) $R_2$ is methyl, ethyl, a methylene group connected to $R_1$ through a single bond such that $R_1$ and $R_2$ form a five-membered ring, or a methylene group connected to $R_1$ through another methylene group such that $R_1$ and $R_2$ form a six-membered ring;

(c) Z is an alkyl or a saturated, unsaturated or aromatic, monocyclic or polycyclic carbocycle or heterocycle containing one or more heteroatoms selected from O, N, or S; and (d) $R_4$ is one or more substituents on Z comprising independently hydrogen, alkoxy, alkylthio, alkyl, alkenyl, amino, carboxyl, cyano, halogen, hydroxy, nitro, and thiol;

(e) or a protected form, salt, pharmaceutically-acceptable salt, biohydrolyzable ester, or solvate thereof; which comprises the steps of:

(I) preparing an intermediate having the general structure:

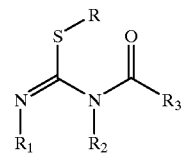

wherein:

(a) R is selected from the group consisting of methyl, ethyl, and benzyl;

(b) $R_1$ is methyl, ethyl, a methylene group connected to $R_2$ through a single bond such that $R_1$ and $R_2$ form a five-membered ring, or a methylene group connected to $R_2$ through another methylene group such that $R_1$ and $R_2$ form a six-membered ring;

(c) $R_2$ is methyl, ethyl, a methylene group connected to $R_1$ through a single bond such that $R_1$ and $R_2$ form a five-membered ring, or a methylene group connected to $R_1$ through another methylene group such that $R_1$ and $R_2$ form a six-membered ring;

(d) $R_3$ is —O—$R_5$ or —$R_6$;

(e) $R_5$ is selected from the group consisting of allyl, methyl, ethyl, benzyl, tert-butyl, and phenyl; and (f) $R_6$ is selected from the group consisting of methyl, ethyl, tert-butyl, and phenyl;

from a thiourea having the general structure:

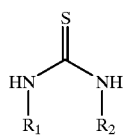

wherein:

(a) $R_1$ is methyl, ethyl, a methylene group connected to $R_2$ through a single bond such that $R_1$ and $R_2$ form a five-membered ring, or a methylene group connected to $R_2$ through another methylene group such that $R_1$ and $R_2$ form a six-membered ring;

(b) $R_2$ is methyl, ethyl, a methylene group connected to $R_1$ through a single bond such that $R_1$ and $R_2$ form a five-membered ring, or a methylene group connected to $R_1$ through another methylene group such that $R_1$ and $R_2$ form a six-membered ring; in a two-step, one-pot reaction by:

a) alkylating the thiourea using an alkylating agent to form a 2-thio-substituted-2-imidazoline, an amidine, or 2-thio-substituted-3,4,5,6-tetrahydropyrimidine;

b) acylating the 2-thio-substituted-2-imidazoline, amidine, or 2-thio-substituted-3,4,5,6-tetrahydropyrimidine of step (I)(a) with an acylating agent in the presence of a base; and (II) coupling the intermediate of step (I) with an amine or its salts of structure:

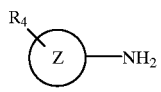

in the presence of an organic acid.

DETAILED DESCRIPTION OF THE INVENTION

The present invention relates to processes for the manufacture of 2-amino-2-imidazoline, guanidine, and 2-amino-3,4,5,6-tetrahydropyrimidine derivatives. Such 2-amino-2-derivatives are useful for treating various medical disorders, including respiratory disorders, ocular disorders, gastrointestinal disorders, nasal decongestion, hypertension, migraine, disorders associated with sympathetic nervous system activity, and substance abuse. When the compounds made according to these processes are used for treating such disorders, they must be pharmaceutically-acceptable. As used herein, such a "pharmaceutically acceptable" component is one that is suitable for use with humans and/or animals without undue adverse side effects (such as toxicity, irritation, and allergic response) commensurate with a reasonable benefit/risk ratio. Such pharmaceutically-acceptable forms include salts, biohydrolyzable esters and solvates.

The 2-amino-2-derivatives prepared according to the processes of the present invention may also be used as intermediates for preparation of other 2-amino-2-derivatives. That is, the compounds prepared may be further reacted, using known chemistry, to yield other active analogs.

DEFINITIONS AND USAGE OF TERMS

The following is a list of definitions for terms used herein:

As used herein, "acylating agent" means a reagent suitable for acylating a nitrogen atom to form a carbamate or an amide, preferably a carbamate. Preferred acylating agents include di-tert-butyl dicarbonate, diethylpyrocarbonate, dimethylpyrocarbonate, methyl chloroformate, ethyl chloroformate, benzyl chloroformate, allyl chloroformate, phenyl chloroformate, acetyl chloride, propionyl chloride, acetic anhydride, propionic anhydride, trimethylacetyl chloride, trimethylacetic anhydride, and benzoyl chloride. More preferred acylating agents are di-tert-butyl dicarbonate, dimethylpyrocarbonate, and methyl chloroformate. The most preferred acylating agent is methyl chloroformate.

As used herein, "alkenyl" means a hydrocarbon substituent with one or more double bonds, straight or branched chain, unsubstituted or substituted.

As used herein, "alkoxy" means a substituent having the structure Q—O—, where Q is alkyl or alkenyl.

As used herein, "alkyl" means a saturated hydrocarbon substituent, straight or branched chain, unsubstituted or substituted.

As used herein, "alkylating agent" means a reagent suitable for alkylating a heteroatom such as sulfur. Preferred alkylating agents include methyl iodide, methyl bromide, methyl chloride, dimethyl sulfate, ethyl iodide, ethyl bromide, ethyl chloride, diethyl sulfate, and benzyl bromide. More preferred alkylating agents include methyl iodide, methyl bromide, dimethyl sulfate, ethyl iodide and diethyl sulfate. The most preferred alkylating agents are methyl iodide and dimethyl sulfate.

As used herein, "alkylthio" means a substituent having the structure Q—S—, where Q is alkyl or alkenyl.

As used herein, "base" means a basic reagent which is added to a reaction mixture to facilitate acylation of nitrogen using an acylating agent. Bases include nitrogen bases and inorganic bases. Preferred bases include those which have easily filterable or otherwise removable salts. Specifically, preferred bases include N,N-diisopropylethylamine, triethylamine, trimethylamine, 4-dimethylaminopyridine, pyridine, potassium carbonate, sodium carbonate, potassium bicarbonate, and sodium bicarbonate. The more preferred bases are triethylamine, trimethylamine, and potassium carbonate. The most preferred base is potassium carbonate.

As used herein, "biohydrolyzable ester" is an ester moiety that does not interfere with the therapeutic activity of the compound, or that is readily metabolized by a human or other mammal.

As used herein, "carbocyclic ring" is a saturated, unsaturated, or aromatic, hydrocarbon ring radical. Carbocyclic rings are monocyclic or are fused, bridged, or spiro polycyclic ring systems. Monocyclic rings contain from 3 to 9 atoms, preferably 4 to 7 atoms, and most preferably 5 or 6 atoms. Polycyclic rings contain from 7 to 17 atoms, preferably from 7 to 14 atoms, and most preferably 9 or 10 atoms.

As used herein, "ether solvent" is a solvent which has two alkyl groups bonded to an oxygen, including those in which the alkyl groups and oxygen atom are part of a ring. Preferred ether solvents include diethyl ether, methyl tert-butyl ether, tetrahydrofuran, and isopropyl ether. More preferred ether solvents include methyl tert-butyl ether and isopropyl ether. The most preferred ether solvent is methyl tert-butyl ether.

As used herein, "halocarbon solvents" are solvents that have one or more halogens attached to a carbon chain. Preferred hydrocarbon solvents include dichloromethane, ethylene dichloride, chloroform, and carbon tetrachloride. More preferred are dichloromethane and ethylene dichloride. Even more preferred is ethylene dichloride.

As used herein, "halogen" is a chloro, bromo, fluoro, or iodo atom radical. Bromo, chloro, and fluoro are preferred halogens.

As used herein, "heterocyclic ring" is a saturated, unsaturated, or aromatic, ring radical comprised of carbon atoms and one or more heteroatoms in the ring. Heterocyclic rings are monocyclic or are fused, bridged, or spiro polycyclic ring systems. Monocyclic rings contain from 3 to 9 atoms, preferably 4 to 7 atoms, and most preferably 5 or 6 atoms. Polycyclic rings contain from 7 to 17 atoms, preferably from 7 to 14 atoms, and most preferably 9 or 10 atoms.

As used herein, "methylene" is a —CH$_2$— radical.

As used herein, "organic acid" is an organic carboxylic acid, such as formic acid, acetic acid, chloroacetic acid, dichloroacetic acid, propionic acid, benzoic acid, maleic acid, fumaric acid, succinic acid, and tartaric acid. Preferred organic acids include acetic acid, propionic acid, and chloroacetic acid. The most preferred organic acid is acetic acid.

As used herein, "polar aprotic solvent" is a solvent that possesses the property of high polarity, yet does not have the ability to donate a proton. Preferred polar aprotic solvents include, acetonitrile, methyl ethyl ketone, N,N-dimethylformamide, N,N-dimethylacetamide, N-methylpyrrolidinone, and methyl sulfoxide. The most preferred polar aprotic solvents are acetonitrile and N,N-dimethylacetamide.

As used herein, "protic solvent" is a solvent that contains a hydrogen atom that is attached to an oxygen or nitrogen atom. Preferred protic solvents include methanol, ethanol, 2-propanol, butanol, sec-butanol, and isoamyl alcohol. The most preferred protic solvents are ethanol and methanol.

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, amino, aminoalkyl (e.g. aminomethyl, etc.), cyano, halogen, alkoxy, alkoxyacyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

COMPOUNDS PREPARED USING THE PRESENT PROCESS

The compounds made by the processes of this invention encompass any of a variety of heteroaryl 2-amino-2-imidazolines, guanidines, and 2-amino-3,4,5,6-tetrahydropyrimidines. These compounds are of the following general structure:

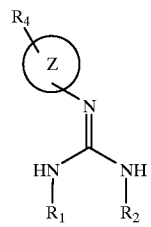

or the tautomers thereof, wherein:

(a) $R_1$ is methyl, ethyl, a methylene group connected to $R_2$ through a single bond such that $R_1$ and $R_2$ form a five-membered ring, or a methylene group connected to $R_2$ through another methylene group such that $R_1$ and $R_2$ form a six-membered ring;

(b) $R_2$ is methyl, ethyl, a methylene group connected to $R_1$ through a single bond such that $R_1$ and $R_2$ form a five-membered ring, or a methylene group connected to $R_1$ through another methylene group such that $R_1$ and $R_2$ form a six-membered ring; and (c) Z is an alkyl or a saturated, unsaturated or aromatic, monocyclic or polycyclic carbocycle or heterocycle containing one or more heteroatoms selected from O, N, or S; and (d) $R_4$ is one or more substituents on Z comprising independently hydrogen, alkoxy, alkylthio, alkyl, alkenyl, amino, carboxyl, cyano, halogen, hydroxy, and thiol;

(e) or a protected form, salt, pharmaceutically-acceptable salt, biohydrolyzable ester, or solvate thereof.

As used herein, $R_1$ and $R_2$ are more preferably methylene groups bonded together either through a single bond or another methylene group to form either a five-membered or a six-membered ring, respectively. Further, it is also more preferable that only $R_1$ or $R_2$ are methyl, the other substituent being ethyl. $R_1$ and $R_2$ are most preferably methylene groups bonded together through a single bond to form a five-membered ring.

As used herein, Z is more preferably an aromatic monocyclic or polycyclic ring. When Z is monocyclic, Z is preferably a five- or six-membered ring and most preferably a six-membered ring. When Z is polycyclic, Z is preferably a six-membered ring fused with either one or two five- or six-membered rings. When Z is polycyclic, Z is most preferably a six-membered ring fused with a five-membered ring.

As used herein, $R_4$ is preferably hydrogen, alkoxy, alkylthio, alkyl, alkenyl, amino, carboxyl, cyano, halogen, hydroxy, nitro, or thiol. $R_4$ is more preferably hydrogen, cyano, alkoxy, alkylthio, amino, $C_1$–$C_4$ alkyl, $C_1$–$C_4$ alkenyl, halogen, or hydroxy. $R_4$ is most preferably hydrogen, cyano, alkoxy, $C_1$–$C_4$ alkyl, $C_1$–$C_4$ alkenyl, or halogen.

Where the compounds synthesized using the present methods are used as intermediates, groups such as amines, imines, or alcohols may be functionalized through methods well known in the art.

The ordinarily skilled artisan will appreciate that tautomeric forms will exist in certain compounds of the invention. When tautomer A of the molecule is shown, it is understood to include tautomers B and C of that molecule although not specifically depicted. To illustrate:

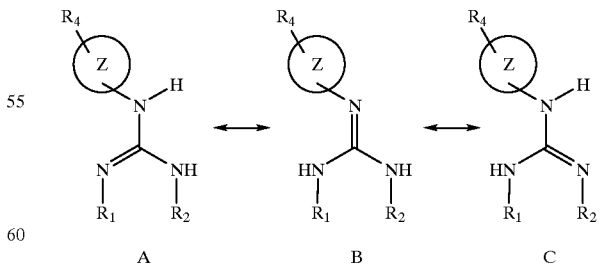

Examples of compounds which may be prepared using the process of the present invention are shown below. These compounds are presented for illustrative purposes only and by no means represent an exhaustive list of possibilities.

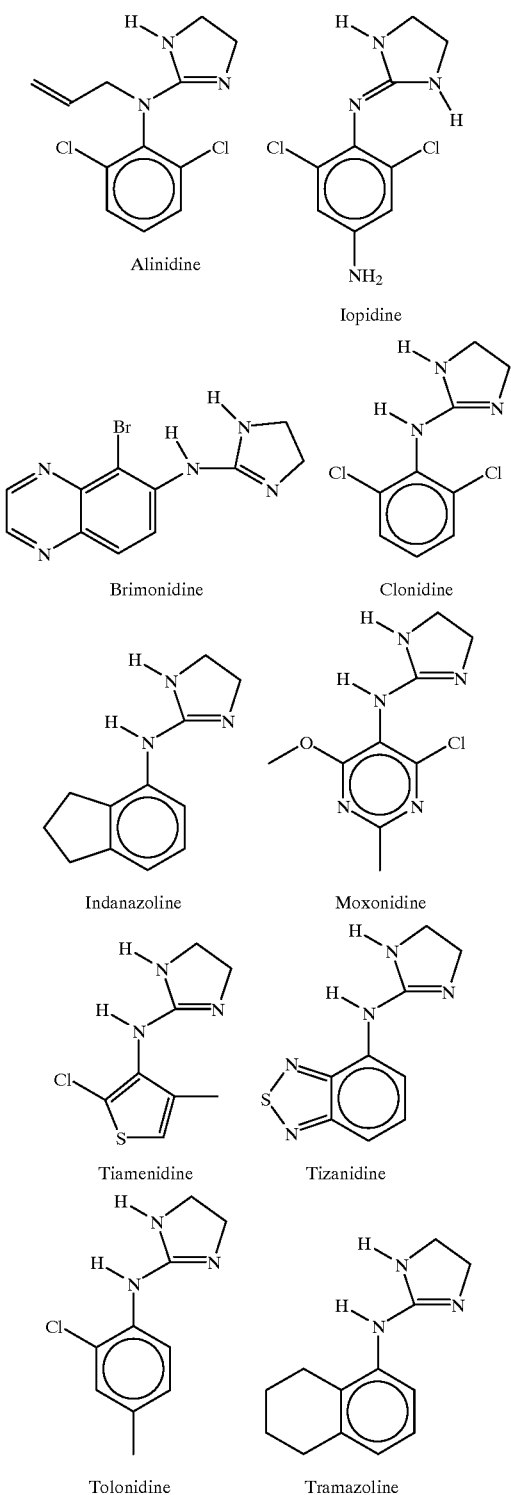

Alinidine

Iopidine

Brimonidine

Clonidine

Indanazoline

Moxonidine

Tiamenidine

Tizanidine

Tolonidine

Tramazoline

The above molecules are disclosed in the following sources which are incorporated herein by reference: Alinidine, disclosed in U.S Pat. No. 3,708,485 (1973) to Boehringer, Ing.; Iopidine, disclosed in U.S. Pat. No. 4,517,199 (1985) to Alcon; Brimonidine, disclosed in German Pat. No. 2,538,620 to Pfizer; Clonidine, disclosed in U.S. Pat. No. 3,202,660 (1965) to Boehringer, Ing.; Indanazoline, disclosed in U.S. Pat. No. 3,882,229 to Nordmark; Moxonidine, U.S. Pat. No. 4,323,570 (1982) to Beiersdorf Aktiengesellschaft; Tiamendine, disclosed in U.S. Pat. No. 3,758,476 (1973) to Hoechst; Tizanidine, disclosed in U.S. Pat. No. 3,843,668 (1974) to Wander-Sandoz; Tolonidine, disclosed in U.S. Pat. No. 3,236,857 (1966) to Boehringer, Ing.; Tramazoline, disclosed in German Pat. No. 1,191,381 (1965) to Thomae.

METHODS OF MANUFACTURE

Generally, the processes of the present invention comprise the novel synthesis of an acylated 2-thio-substituted-2-imidazoline, -amidine, or -3,4,5,6-tetrahydropyrimidine intermediate (hereinafter described as the "acylated intermediate") followed by coupling of the acylated intermediate with an appropriate amine or its salts in the presence of an organic acid. The acylated intermediate used in the synthesis is conveniently prepared in a novel two-step, one-pot reaction from the appropriate thiourea in high yields.

This process is illustrated by the following general scheme:

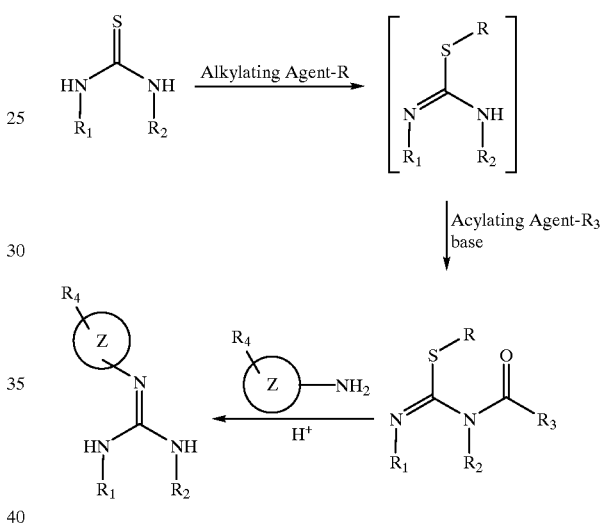

In the above general scheme:

(a) $R_1$ is methyl, ethyl, a methylene group connected to $R_2$ through a single bond such that $R_1$ and $R_2$ form a five-membered ring, or a methylene group connected to $R_2$ through another methylene group such that $R_1$ and $R_2$ form a six-membered ring;

(b) $R_2$ is methyl, ethyl, a methylene group connected to $R_1$ through a single bond such that $R_1$ and $R_2$ form a five-membered ring, or a methylene group connected to $R_1$ through another methylene group such that $R_1$ and $R_2$ form a six-membered ring; and $R_1$ and $R_2$ are more preferably methylene groups bonded together either through a single bond or another methylene group to form either a five-membered or a six-membered ring, respectively. $R_1$ and $R_2$ are most preferably methylene groups bonded together through a single bond to form a five-membered ring.

In the above general scheme, R is an alkyl or aromatic substituent derived from the alkylating agent used in the process. R is preferably a methyl, ethyl, or benzyl radical. R is most preferably a methyl radical.

In the above general scheme, $R_3$ is derived from the acylating agent used in the process. $R_3$ may be —O—$R_5$, or —$R_6$, wherein $R_5$ and $R_6$ are also derived from the acylating agent used in the process. $R_3$ is preferably —O—$R_5$.$R_5$ is preferably an allyl, methyl, ethyl, benzyl, tert-butyl, or phenyl radical. $R_5$ is most preferably a methyl radical. $R_6$ is preferably a methyl, ethyl, tert-butyl, or phenyl radical.

In the above general scheme, Z is an alkyl or a saturated, unsaturated or aromatic, monocyclic or polycyclic carbocycle or heterocycle containing one or more heteroatoms selected from O, N, or S. Z is preferably an aromatic monocyclic or polycyclic ring. When Z is monocyclic, Z is preferably a five- or six-membered ring and most preferably a six-membered ring. When Z is polycyclic, Z is preferably a six-membered ring fused with either one or two five- or six-membered rings. When Z is polycyclic, Z is most preferably a six-membered ring fused with a five-membered ring.

In the above general scheme, $R_4$ is one or more substituents on Z comprising independently hydrogen, alkoxy, alkylthio, alkyl, alkenyl, amino, carboxyl, cyano, halogen, hydroxy, nitro, and thiol. $R_4$ is more preferably hydrogen, cyano, alkoxy, alkylthio, amino, $C_1$–$C_4$ alkyl, $C_1$–$C_4$ alkenyl, halogen, or hydroxy. $R_4$ is most preferably hydrogen, cyano, alkoxy, $C_1$–$C_4$ alkyl, $C_1$–$C_4$ alkenyl, or halogen.

In the above general scheme, a thiourea is reacted with an alkylating agent in a solvent that will allow the alkylation reaction to proceed. More preferred alkylating agents include methyl iodide, methyl bromide, dimethyl sulfate, ethyl iodide and diethyl sulfate. The most preferred alkylating agents are methyl iodide and dimethyl sulfate. Preferred solvents include ester solvents (such as, for example, butyl acetate, ethyl acetate, or methyl acetate, preferably ethyl acetate), ether solvents, protic solvents, and polar aprotic solvents. More preferred solvents include ether solvents, protic solvents and polar aprotic solvents. The most preferred solvents are protic solvents. The most preferred solvent is ethanol. The mixture is allowed to proceed at a temperature preferably between about 0° C. and about 150° C., more preferably between ambient temperature and about 100° C., and most preferably between about 30° C. and about 70° C.

The thio-substituted compound so obtained can be isolated by methods obvious to those who are skilled in the art, such as using methods including extraction, solvent evaporation, distillation, or crystallization procedures. Most preferably, the 2-thio-2-substituted derivative is further reacted in the same vessel and in the same solvent without isolation. Prior to further reaction of the 2-thio-2-substituted derivative, the reaction mixture is preferably cooled from about −10° C. to about 75° C., more preferably cooled from about 0° C. to about 40° C., and most preferably cooled to ambient temperature.

The 2-thio-2-substituted derivative is then reacted with an acylating agent in the presence of a base, in any solvent that allows the reaction to proceed. Preferred acylating agents include di-tert-butyl dicarbonate, diethylpyrocarbonate, dimethylpyrocarbonate, methyl chloroformate, ethyl chloroformate, allyl chloroformate, phenyl chloroformate, acetyl chloride, propionyl chloride, acetic anhydride, propionic anhydride, trimethylacetyl chloride, trimethylacetic anhydride, and benzoyl chloride. More preferred acylating agents are di-tert-butyl dicarbonate, dimethylpyrocarbonate, methyl chloroformate, and acetic anhydride. The most preferred acylating agent is methyl chloroformate. Preferred bases include those which have easily filterable or otherwise removable salts. Specifically, the more preferred bases are triethylamine and potassium carbonate. The most preferred base is potassium carbonate. Preferred solvents include ester solvents (such as, for example, butyl acetate, ethyl acetate, or methyl acetate, preferably ethyl acetate), ether solvents, protic solvents, and polar aprotic solvents. More preferred solvents include ether solvents, protic solvents (particularly ethanol and isopropanol) and polar aprotic solvents (particularly N,N-dimethylacetamide). The most preferred solvents are protic solvents. The most preferred solvent is ethanol. The base is preferably added to the reaction mixture first, followed by the acylating agent, maintaining the temperature of the mixture preferably between about 0° C. to about 50° C., more preferably between about 20° C. to about 35° C. The reaction is allowed to proceed at a temperature preferably between about 20° C. to about 60° C., more preferably between about 40° C. to about 55° C.

Upon completion of the reaction, the acylated intermediate so obtained can be isolated by methods known to those who are skilled in the art, such as methods including extraction, solvent evaporation, distillation or crystallization procedures. More preferably, the reaction mixture is filtered to remove the by-product salts, at a temperature between about 30° C. to about 70° C., more preferably between about 50° C. to about 60° C. The by-product salts are then preferably rinsed with ester solvents (such as, for example, butyl acetate, ethyl acetate, or methyl acetate, preferably ethyl acetate), protic solvents, or polar aprotic solvents, more preferably with a protic or ester solvent. After filtration, the acylated intermediate so obtained can be isolated by methods known to those who are skilled in the art, such as using methods including extraction, solvent evaporation, distillation, or crystallization procedures. Preferably, the product is isolated as a solid, by cooling the filtrate to a temperature from about −30° C. to ambient temperature, more preferably from about −20° C. to about 0° C. The solid so obtained is filtered and rinsed with a protic or ester solvent that has been pre-cooled to between about −30° C. to ambient temperature, more preferably between about −20° C. to about 20° C. The solid is preferably dried by methods known to those who are skilled in the art.

The acylated intermediate can then be further reacted with the appropriate amine or its salts in a protic solvent or a polar aprotic solvent or mixtures thereof, in the presence of an organic acid. The acylated intermediate may also be further reacted with the appropriate amine or its salts in a solution of the organic acid alone. Preferred acids include formic acid, acetic acid, chloroacetic acid, dichloroacetic acid, propionic acid, benzoic acid, maleic acid, fumaric acid, succinic acid, or tartaric acid. The preferred protic solvents include methanol and ethanol. The most preferred polar aprotic solvent is acetonitrile. The reaction is preferably carried out at a temperature between ambient temperature and about 150° C., more preferably between about 40° C. to about 100° C., and even more preferably between about 55° C. to about 80° C. In some cases, wherein $R_3$ is not readily removable, it may be necessary to add an inorganic acid such as HCl or HBr, additional amounts of an organic acid, or a more protic solvent, and/or apply increased heating to the reaction mixture to facilitate cleavage of the acyl group. Those skilled in the art will recognize that hydrolysis of this acyl group may also be achieved under basic conditions as well. Upon completion of the reaction, the 2-amino-2-derivative so obtained can be isolated by methods known to those who are skilled in the art, such as methods including extraction, solvent evaporation, distillation or crystallization procedures. Those skilled in the art will also recognize that various acids may be added in the final stages of the process to form various salt forms which may facilitate isolation and handling.

The following non-limiting examples illustrate the processes of the present invention:

EXAMPLE 1

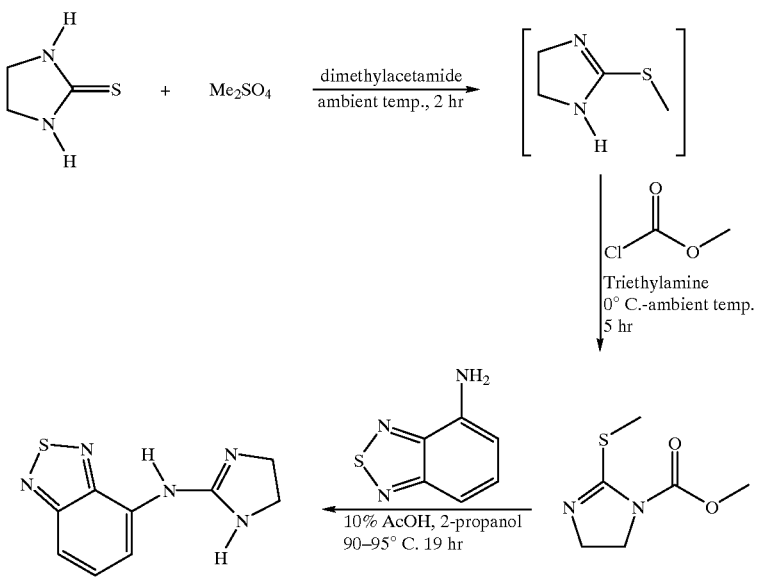

a. 2-Thiomethyl-2-Imidazoline

2-Imidazolidinethione (150 grams, 1.5 mol) and N,N-dimethylacetamide (1.1 L) are combined together in a round-bottom flask. To this is added dimethyl sulfate (213 grams, 1.7 mol) at ambient temperature. This reaction is stirred for two hours.

b. N-Carbomethoxy-2-thiomethyl-2-imidazoline

The reaction mixture of step (a) is cooled in an ice bath and to this stirred solution is added triethylamine (376 grams, 3.7 mol) in a dropwise manner. To this mixture is added methyl chloroformate (166.7 grams, 1.8 mol) in a dropwise manner. After completion of addition, the reaction mixture is allowed to warm to ambient temperature. After 5 hours of stirring, the mixture is poured into cold water (3 L). The product is extracted into ethyl acetate (4×2.5 L). The combined extracts are washed with cold water, brine, dried over sodium sulfate, and concentrated under reduced pressure. Drying the residue under vacuum affords the desired N-carbomethoxy-2-thiomethyl-2-imidazoline.

c. 4-(2-Imidazolinylamino)-1,3,2-benzothiadiazole, acetate salt

N-Carbomethoxy-2-thiomethyl-2-imidazoline (19.2 grams, 11 mmol) and 4-amino-2,1,3-benzothiadiazole (11.1 grams, 73 mmol) are dissolved in a 10% solution of glacial acetic acid in 2-propanol (500 mL). The resulting solution is heated near reflux (90–95° C.) for 19 hours. The mixture is concentrated under reduced pressure, redissolved in 2-propanol and reprecipitated to yield 4-(2-imidazolinylamino)-1,3,2-benzothiadiazole, acetate salt.

EXAMPLE 2

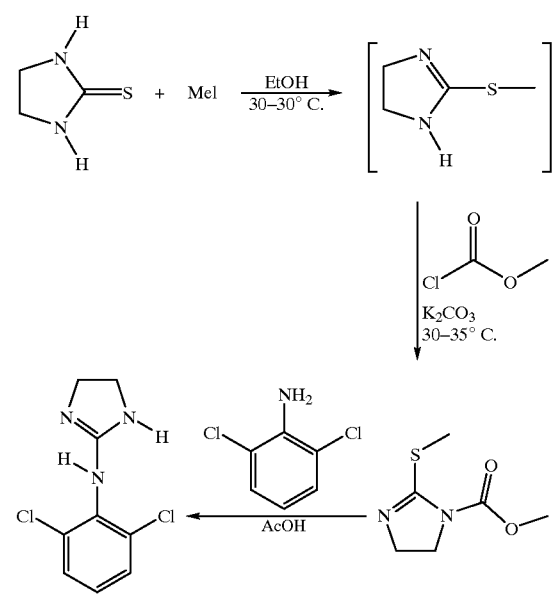

a. 2-Thiomethyl-2-imidazoline

2-Imidazolidinethione (50 grams) and absolute ethanol (400 mL) are combined while stirring. Methyl iodide (43 mL, 1.4 eq.) is rapidly added to the stirring mixture. The reaction mixture is then warmed to 35° C. until the formation of 2-thiomethyl-2-imidazoline is complete.

b. N-Carbomethoxy-2-thiomethyl-2-imidazoline

Potassium carbonate (101 grams) is added to the mixture in step (a) above, followed by addition of methyl chloroformate (42 mL) while stirring. After 45 minutes, the reaction mixture is heated to 55° C. and the insoluble salts are filtered off. These salts are washed with absolute ethanol. The filtrate (and ethanol wash) are cooled to −20° C. and the final product is isolated by filtration. The final product is washed with cold (−20° C.) absolute ethanol. The product is dried overnight under vacuum at room temperature, giving N-carbomethoxy-2-thiomethyl-2-imidazoline.

c. 2-[(2,6-Dichlorophenyl)amino]-2-imidazoline, acetate salt 2,6-Dichloroaniline (2 g) and N-carbomethoxy-2-thiomethyl-2-imidazoline (2.68 g) are dissolved in glacial acetic acid (40 mL), and the reaction is stirred at 65 to 75° C. until coupling step is complete. The reaction mixture is diluted with 70% methanol-water (40 ml), refluxed until deprotection is complete, and then concentrated under reduced pressure to furnish an oily residue. Addition of ethyl acetate to the oily residue precipitates the impurities which are separated by filtration. Concentration of the filtrate provides 2-[(2,6-dichlorophenyl)amino]-2-imidazoline as an acetate salt.

EXAMPLE 3

Potassium carbonate (101 grams) is added to the mixture in step (a) above. Methyl chloroformate (42 mL, 540 mmol) is then added. After 1 hour, the reaction mixture is heated to 55° C. and the insoluble salts are filtered. The salts are washed with ethanol (100 mL). The filtrate (and ethanol wash) are cooled to −20° C. and the final product is isolated by filtration. The final product is washed with 100 mL cold (−20° C.) absolute ethanol. The 2-thiomethylamidine is dried overnight under vacuum at ambient temperature.

c. N,N'-Dimethyl-N"-(8-methylquinolin-7-yl)guanidine, acetate salt

The intermediate prepared in step (b) above is combined with 0.7 equivalents of 7-amino-8-methylquinoline (prepared in U.S. Pat. No. 5,576,437 issued to Cupps and Bogdan, Nov. 19, 1996 (incorporated herein by reference) in a 10% solution of glacial acetic acid in ethanol (2 L). The mixture is heated to reflux and after the starting amine is

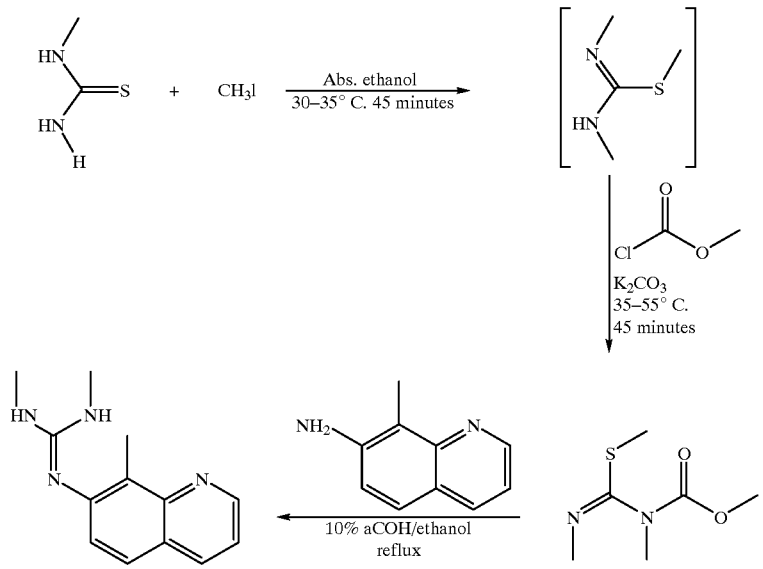

a. N,N-Dimethyl-(2-thiomethyl)amidine

To 1,3-dimethyl-2-thiourea (50 grams, 480 mmol) is added absolute ethanol (400 mL) with stirring. Iodomethane (43 mL, 690 mmol) is added rapidly. The reaction mixture is warmed to 30–35° C. and is stirred until the formation of N,N'-dimethyl-(2-thiomethyl)amidine is complete.

b. N,N'-Dimethyl-(N-methoxycarbonyl-2-thiomethyl) amidine consumed, the mixture is decolorized with deactivated carbon. The product is cooled to ambient temperature, filtered, dried, and recrystallized from acetonitrile and water. Upon drying under high vacuum, N,N'-Dimethyl-N"-(8-methylquinolin-7-yl)guanidine, acetate salt is obtained.

EXAMPLE 4

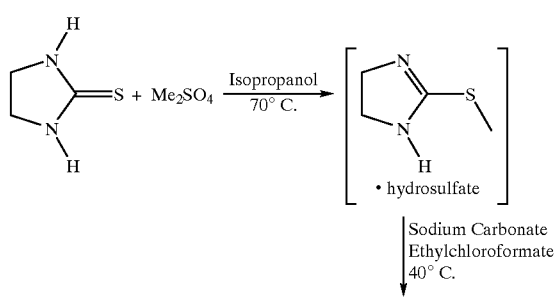

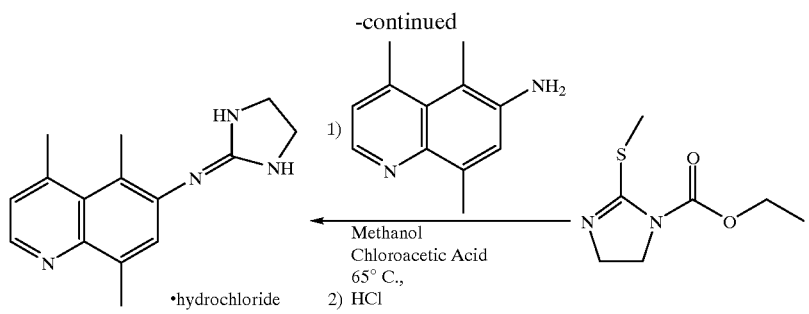

a. 2-Thiomethyl-2-imidazoline

Dimethylsulfate (111 mL) is slowly added to a stirred solution of 2-imidazolidinethione (120 g) in isopropanol (750 mL) at ambient temperature. The reaction mixture is heated to 70° C. until the formation of 2-thiomethyl-2-imidazoline hydrosulfate is complete.

b. N-Carboethoxy-2-thiomethyl-2-imidazoline

The reaction mixture of step (a) is allowed to cool to ambient temperature, whereupon sodium carbonate (249 g) is added, followed by the addition of ethylchloroformate (168 mL). The reaction mixture is stirred at 40° C. until complete, whereupon the reaction mixture is heated to 55° C. and the hot mixture is filtered to remove the insoluble salts. These salts are washed with cold isopropanol. The filtrate (and wash solution) is cooled to −20° C. and stirred for 2 hours. The solid obtained is filtered off and washed with cold water and then cold absolute ethanol. The product is dried under vacuum at room temperature to provide N-Carboethoxy-2-thiomethyl-2-imidazoline as a solid.

c. 6-(2-Imidazolinylamino)-4,5,8-trimethylquinoline, hydrochloride salt

6-Amino-4,5,8-trimethylquinoline (115.5 g) (as prepared in Example 2 of copending U.S. patent application Ser. No. 08/169,343) and N-carboethoxy-2-thiomethyl-2-imidazoline (140 g), is dissolved in 10% chloroacetic acid in methanol (2.8 L, w/w) and stirred at 65° C. until complete.

The reaction mixture is cooled to room temperature and HCl gas is added. The reaction mixture is stirred for 2 hours and then cooled to −20° C. and stirred until the product completely precipitates. The crude product so obtained is filtered, recrystallized from ethanol/water and dried (vacuum, 40° C.) to provide the desired, purified 6-(2-imidazolinylamino)-4,5,8-trimethylquinoline, hydrochloride salt.

EXAMPLE 5

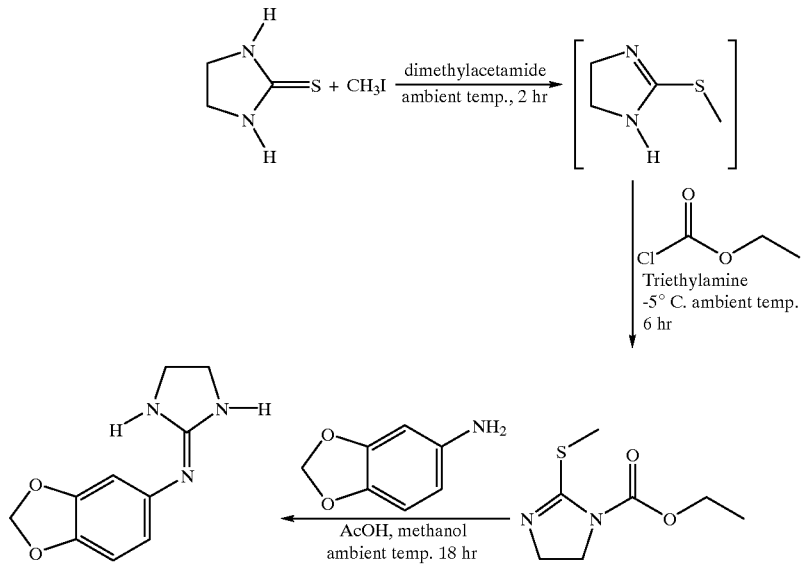

a. 2-Thiomethyl-2-Imidazoline

2-Imidazolidinethione (68 grams, 670 mmol) and N,N-dimethylacetamide (700 mL) are combined together in a round-bottom flask. To this is added iodomethane (50 mL, 810 mmol) at ambient temperature. This reaction is allowed to stir for two hours.

b. N-Carboethoxy-2-thiomethyl-2-imidazoline

The reaction mixture is cooled in an ice bath and to this stirred solution is added triethylamine (250 mL, 1.8 mol) in a dropwise manner. To this mixture is added ethyl chloroformate (81 mL, 850 mmol) in a dropwise manner at −5° C. Five minutes after completion of addition, the reaction mixture is allowed to warm to ambient temperature and is then stirred for 6 hours. The reaction is poured into ice cold water (4 L). The product is extracted into ethyl acetate (4×2.5 L). The combined extracts are washed with cold water (3×2 L), brine (2 L), dried over sodium sulfate, and concentrated under reduced pressure to give an oily residue. Drying the residue under vacuum affords the desired N-carboethoxy-2-thiomethyl-2-imidazoline.

c. 2-(1',3'-Benzodioxolyl-5'-amino)imidazoline

N-Carboethoxy-2-thiomethyl-2-imidazoline (22.5 grams, 104 mmol) is dissolved in methanol (1 L) and to this is added glacial acetic acid (12 mL, 208 mmol). The reaction mixture is allowed to stir for 10 minutes. To this solution is added 3,4-(methylenedioxy)aniline (14.3 grams, 104 mmol) and the reaction is allowed to stir at ambient temperature until the reaction is complete. The solvent is removed under reduced pressure. The crude product is extracted into ethyl acetate, dried, and evaporated to give 2-(1',3'-benzodioxolyl-5'-amino)imidazoline.

EXAMPLE 6

The reaction mixture of step (a) above is allowed to cool to ambient temperature. Triethylamine is then added to the stirring mixture (14 mL). To this solution at room temperature is added 4-dimethylaminopyridine (12.2 grams, 100 mmol) and then di-tert-butyldicarbonate (65.4 grams, 300 mmol). The reaction is allowed to stir for 6 hours. The solvent is removed under reduced pressure leaving a solid which is further dried under vacuum. The crude material is extracted into ethyl acetate, washed with water, dried, and evaporated to give the pure N-t-butoxycarbonyl-2-thiomethyl-2-imidazoline.

c. 5-(2-Imidazolinylamino)-benzimidazole, hydrobromide salt

5-Aminobenizimidazole (5 grams, 38 mmol) and N-t-butoxycarbonyl-2-thiomethyl-2-imidazoline (9.4 grams, 42 mmol) are dissolved in 10% acetic acid in methanol (400 mL) and are stirred for 24 hours at ambient temperature. To this solution is added 30% HBr/AcOH (100 mL) and the reaction is stirred for an additional 4 hours. The resulting solution is concentrated under reduced pressure, redissolved in methanol and recrystallized from methanol/diethyl ether to yield the desired product as the hydrobromide salt.

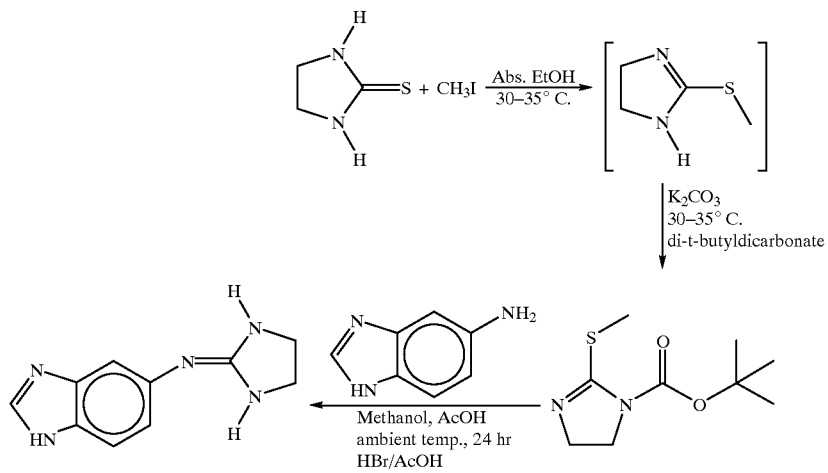

a. 2-Thiomethyl-2-imidazoline

2-Imidazolidinethione (10.2 grams, 100 mmol) and dichloromethane (400 ml) are combined in a round-bottom flask equipped with a reflux condenser, with stirring. Iodomethane (8.7 mL, 140 mmol) is rapidly added. The reaction mixture is warmed to 30° C. –35° C. until the formation of 2-thiomethyl-2-imidazoline is complete.

b. N-t-Butoxycarbonyl-2-thiomethyl-2-imidazoline

EXAMPLE 7

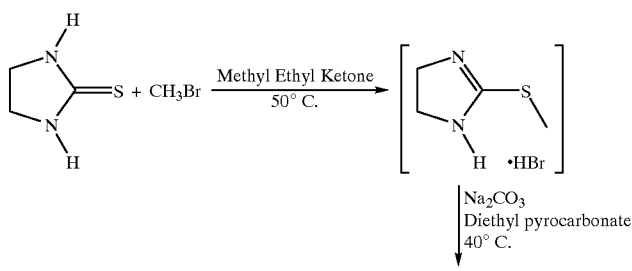

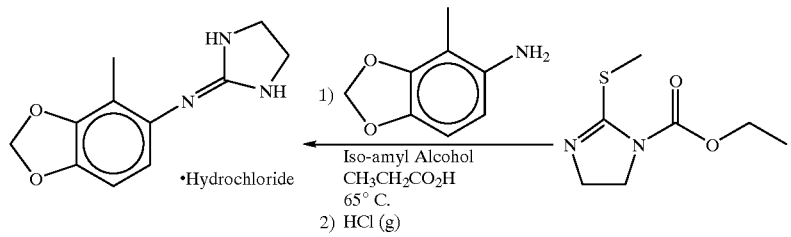

a. 2-Thiomethyl-2-imidazoline

In a pressure reactor, methyl bromide (32 g) is slowly added to a solution of 2-imidazolidinethione (17 g) in methyl ethyl ketone (175 mL) with stirring at ambient temperature. The reaction mixture is heated to 65° C. under pressure, until the formation of 2-methylthio-2-imidazoline hydrobromide is complete.

b. N-Carboethoxy-2-thiomethyl-2-imidazoline

The reaction mixture of step (a) is allowed to cool to ambient temperature and the excess methyl bromide is released and trapped. To this mixture is added sodium carbonate (26.5 g), followed by the addition of diethyl pyrocarbonate (42 mL). The reaction mixture is stirred at 40° C. until complete, whereupon the reaction mixture is heated to 55° C. and the hot solution is filtered to remove the insoluble salts. These salts are washed with cold absolute ethanol. The filtrate (and ethanol wash) is cooled to −20° C. and stirred for 2 hours. The solid obtained is filtered, and washed with cold water and then cold absolute ethanol. The product is dried under vacuum at room temperature to provide N-carboethoxy-2-thiomethyl-2-imidazoline as a solid.

c. 5-(2-Imidazolinylamino)4-methyl-1,3-benzodioxole, hydrochloride salt

5-Amino-4-methyl-1,3-benzodioxole (13.25 g) (as prepared in application Ser. No. 08/478,708) and N-carboethoxy-2-thiomethyl-2-imidazoline (20 g) are dissolved in 10% propionic acid in isoamyl alcohol (325 mL, w/w) and the reaction mixture is stirred at 65° C. until complete. The reaction mixture is cooled to room temperature and HCl gas (13 g) is slowly added. The mixture is stirred for an additional 2 hours, whereupon it is then cooled to −20° C. and stirred until the product precipitates. The crude product obtained is filtered, recrystallized from methanol/diethyl ether and dried (vacuum, 40° C.) to provide the desired, purified 5-(2-imidazolinylamino)4methyl-1,3-benzodioxole, hydrochloride salt.

EXAMPLE 8

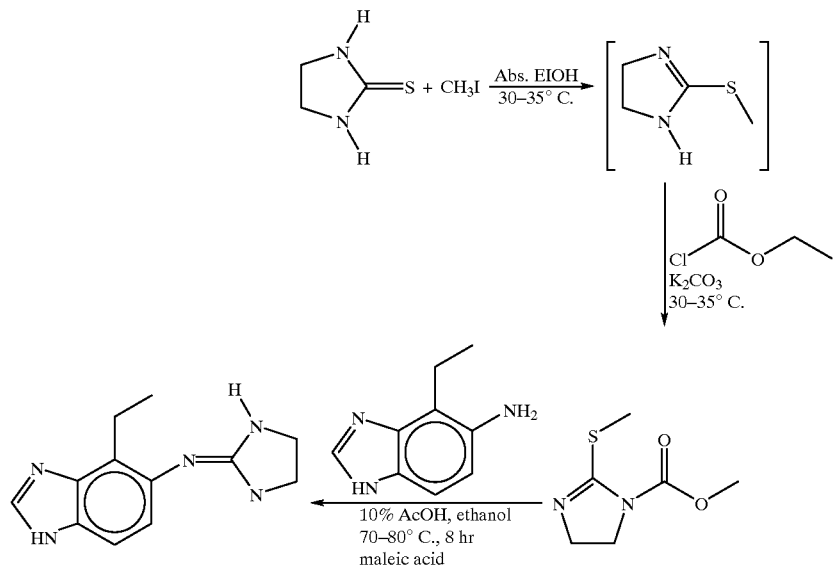

a. 2-Thiomethyl-2-imidazoline

2-Imidazolidinethione (50 grams) and absolute ethanol (400 mL) are combined while stirring. Methyl iodide (43 mL, 1.4 Eq) is rapidly added to the stirring mixture. The reaction mixture is then warmed to 35° C. until the formation of 2-thiomethyl-2-imidazoline is complete.

b. N-Carbomethoxy-2-thiomethyl-2-imidazoline

Potassium carbonate (101 grams) is added to the mixture in step (a) above, followed by addition of methyl chloroformate (42 mL) while stirring. After 45 minutes, the reaction mixture is heated to 55° C. and the insoluble salts are filtered off. These salts are washed with absolute ethanol. The filtrate (and ethanol wash) are cooled to −20° C. and the final product is isolated on a filter. The final product is washed with cold (−20° C.) absolute ethanol. The product is dried overnight under vacuum at room temperature, giving N-carbomethoxy-2-thiomethyl-2-imidazoline.

c. 4-Ethyl-5-(2-imidazolinylamino)benzimidazole, maleate salt

The N-Carbomethoxy-2-thiomethyl-2-imidazoline (23.8 grams, 140 mmol) is combined with 5-amino-4-ethylbenzimidazole (20 grams, 124 mmol) (prepared by deprotecting tert-butoxycarbonyl protecting group of intermediate prepared in U.S. Pat. No. 5,478,858 issued to Cupps and Bogdan, Dec. 26, 1995 (incorporated herein by reference), under standard deprotection conditions known in the art) and a 10% solution of acetic acid in ethanol (500 mL) in a flask equipped with a reflux condenser. This mixture is stirred for 1 hour. The mixture is then heated at 65° C. for 12 hours. At this time, the reaction is cooled to ambient temperature and maleic acid (48 grams, 410 mmol) is added. The resulting mixture is stirred for two hours and then is cooled to 0° C. The mixture is stirred until the product completely precipitates (approximately 1 hour), whereupon the mixture is filtered. The crude product is washed with cold ethanol and then recrystallized from acetonitrile/water to give 4-ethyl-5-(2-imidazolinylamino) benzimidazole, maleate salt.

EXAMPLE 9 b. N-3-Carbomethoxy-2-thiomethyl-4,5,6-tetrahydropyrimidine

The mixture in step (a) above is cooled to ambient temperature and potassium carbonate (178 g) is added, followed by addition of methyl chloroformate (73.2 mL) while stirring. The reaction mixture is stirred at 40° C. until complete, whereupon the reaction mixture is heated to 55° C. and the hot solution is filtered to remove the insoluble salts. These salts are washed with cold absolute ethanol. The filtrate (and ethanol wash) is cooled to −20° C. and stirred for 2 hours. The solid obtained is filtered, and washed with cold water and then cold absolute ethanol. The product is dried under vacuum at room temperature to provide N-3-carbomethoxy-2-thiomethyl-4,5,6-tetrahydropyrimidine.

c. 2-(5-Methyl-6-quinoxalinylamino)3,4,5,6-tetrahydropyrimidine

6-Amino-5-methylquinoxaline (73.8 g) (as prepared in copending U.S. patent application Ser. No.08/478,708) and N-3-carbomethoxy-2-thiomethyl4,5,6-tetrahydropyrimidine (113.5 g) are dissolved in 10% acetic acid in ethanol (1.1 L) and stirred at 65° C. until complete. The reaction mixture is

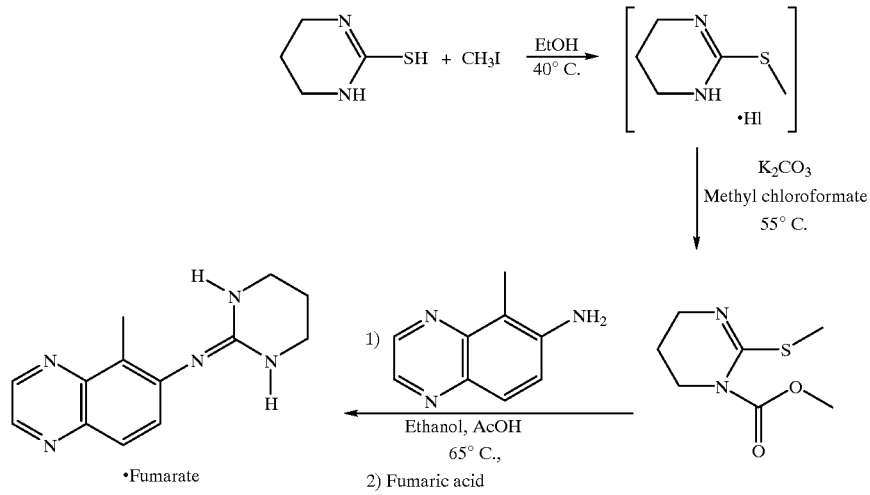

a. 2-Thiomethyl-3,4,5,6-tetrahydropyrimidine

Methyl iodide (75 mL) is slowly added to a stirred solution of 3,4,5,6-tetratydro-2-pyrimidine thiol (100 g) in ethanol (600 mL) at ambient temperature. The reaction mixture is heated to 40° C. until the formation of 2-thiomethyl-3,4,5,6-tetrahydropyrimidine hydroiodide is complete.

cooled to ambient temperature and fumaric acid is added (189 g). The mixture is stirred for 2 hours and then cooled to −20° C. and stirred until the product has completely precipitatated. The crude product so obtained is recrystallized from acetonitrile/water to provide the desired, purified 2-(5-Methyl-6-quinoxalinylamino)3,4,5,6-tetrahydropyrimidine, fumarate salt.

EXAMPLE 10

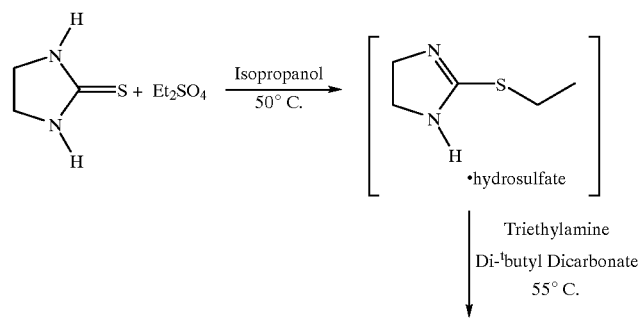

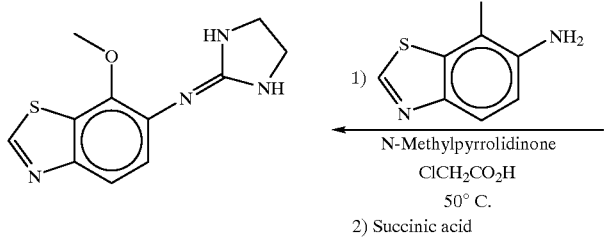
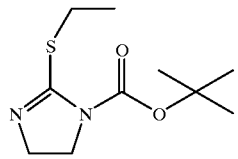

a. 2-Thioethyl-2-imidazoline hydrosulfate

Diethyl sulfate (47.75 mL) is slowly added to a solution of 2-imidazolidinethione (30 g) in isopropanol (250 mL) with stirring at ambient temperature. The reaction mixture is heated to 50° C. until the formation of 2-thioethyl-2-imidazoline hydrosulfate is complete.

b. N-tert-butoxycarbonyl-2-thioethyl-2-imidazoline

The reaction mixture of step (a) is allowed to cool to ambient temperature, whereupon triethylamine (105 mL) and then di-tert-butyldicarbonate (74.25 mL) are added. The reaction mixture is heated to 55° C. and stirred until complete. The reaction mixture is then filtered hot, removing the insoluble salts. These salts are washed with cold isopropanol. The filtrate (and isopropanol wash) is cooled to −20° C. and and stirred for 2 hours. The solid obtained is filtered and washed with water and cold absolute ethanol. The product is dried under vacuum at room temperature to provide N-tert-butoxycarbonyl-2-thioethyl-2-imidazoline as a solid.

c. 5-(2-Imidazolinylamino)-4-methoxybenzothiazole, succinate salt

5-Amino-4-methoxybenzothiazole (18 g) (as prepared in Example 5 of copending U.S. patent application Ser. No. 60/031,756) and N-tert-butoxycarbonyl-2-thioethyl-2-imidazoline (32.5 g) are dissolved in 10% chloroacetic acid in N-methylpyrrolidinone (390 mL, w/w). The mixture is then stirred at 50° C. until the reaction is complete. The mixture is cooled to ambient temperature and succinic acid (47.5 g) is added, and the mixture is stirred for an additional 4 hours. The resulting solution is cooled to −20° C. and stirred until the product completely precipitates. The crude product is then filtered and recrystallized from ethanol/water to provide the desired, purified salt of 5-(2-imidazolinylamino)4-methoxybenzothiazole.

EXAMPLE 11

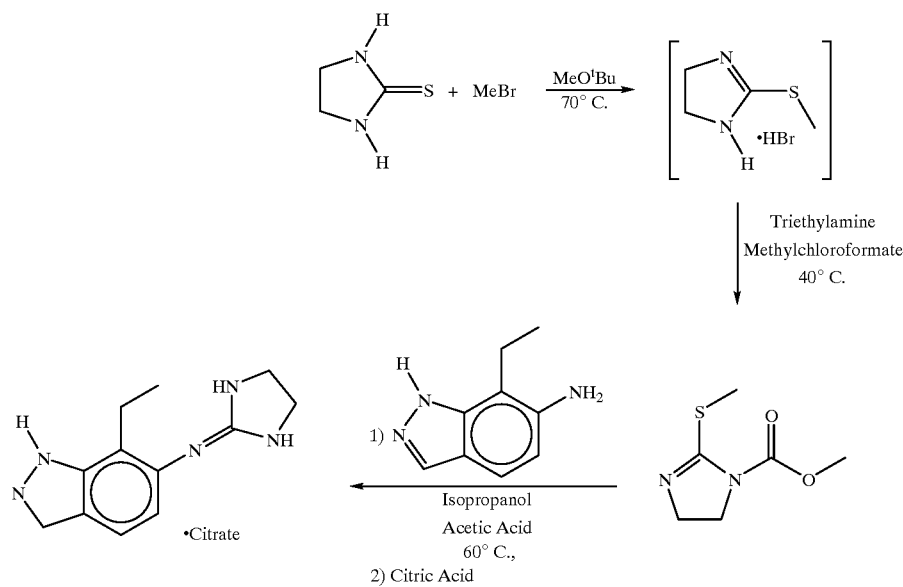

a. 2-Thiomethyl-2-imidazoline hydrobromide

In a pressure reactor, methyl bromide (20.5 g) is slowly added to a stirred solution of 2-imidazolidinethione (15 g) in methyl tert-butyl ether (120 mL) at ambient temperature. The reaction mixture is heated to 70° C., under pressure, until the formation of 2-thiomethyl-2-imidazoline hydrobromide is complete.

b. N-Carbomethoxy-2-thiomethyl-2-imidazoline

The reaction mixture of step (a) is allowed to cool to ambient temperature and the excess methyl bromide is released and trapped. To this mixture is added triethylamine (53.2 mL), followed by the addition of methylchloroformate (13.6 mL). The reaction mixture is stirred at 40° C. until complete, whereupon the reaction mixture is heated to 55° C. and the hot solution is filtered to remove the insoluble salts. These salts are washed with cold methyl tert-butyl ether. The filtrate (and wash solution) is cooled to −20° C. and stirred for 2 hours. The solid obtained is filtered, and washed with cold water and then cold absolute ethanol. The product is dried overnight under vacuum at room temperature to provide N-carbomethoxy-2-thiomethyl-2-imidazoline as a solid.

c. 7-Ethyl-6-(2-imidazolinylamino)indazole, citrate salt

6-Amino-7-ethylindazole (9.9 g) (as prepared in Example 1 of copending U.S. patent application Ser. No. 60/031,740) and N-carbomethoxy-2-thiomethyl-2-imidazoline (14 g) are dissolved in 10% acetic acid in isopropanol (210 mL, w/v) and stirred at 60° C. until the reaction is complete. The reaction mixture is cooled to ambient temperature and citric acid (41.5 g) is added. The resulting mixture is stirred for 2 hours. The solution is cooled to −20° C. and stirred until the product has completely precipitated. The crude product so obtained is filtered, recrystallized from ethanol/water, and dried (vacuum, 40° C.) to provide the desired, purified 7-ethyl-6-(2-imidazolinylamino)indazole, citrate salt.

EXAMPLE 12 g) is added, followed by the addition of dimethyl pyrocarbonate (442 mL). The reaction mixture is heated to 55° C. and stirred until complete. The hot solution is filtered to remove the insoluble salts. These salts are washed with cold absolute ethanol. The filtrate (and ethanol wash) is cooled to −20° C. and stirred for 2 hours. The solid obtained is filtered, and washed with cold water, followed by cold absolute ethanol. The product is dried under vacuum at room temperature to provide N-carbomethoxy-2-thiomethyl-2-imidazoline as a solid.

c. 3-Cyano-6-(2-imidazolinylamino)-7-methylindole, hydrobromide salt

6-Amino-3-cyano-7-methylindole (34 g) (as prepared in Example 3 of copending U.S. patent application Ser. No. 60/031,774) and N-carbomethoxy-2-thiomethyl-2-imidazoline (38 g), are dissolved in 10% chloroacetic acid in N,N-dimethylformamide (480 mL, w/w) and stirred at 50° C. until the reaction is complete. This solution is cooled to ambient temperature and 30% HBr in acetic acid (140 mL)

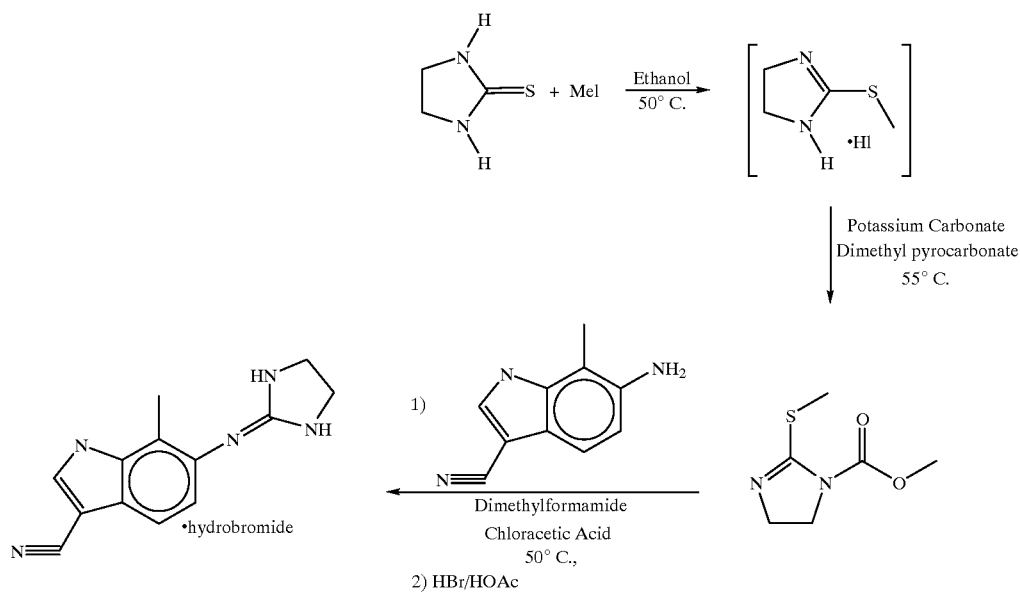

a. 2-Thiomethyl-2-imidazoline hydroiodide

Methyl iodide (91 mL) is slowly added to a solution of 2-imidazolidinethione (210 g) in ethanol (1.2 L) with stirring at ambient temperature. The reaction mixture is heated to 40° C. until the formation of 2-thiomethyl-2-imidazoline hydroiodide is complete.

b. N-Carbomethoxy-2-thiomethyl-2-imidazoline

The reaction mixture of step (a) is allowed to cool to ambient temperature, whereupon potassium carbonate (426 is added, and the mixture is stirred for an additional 4 hours. The resulting solution is cooled to −20° C. and stirred until the product precipitates. The crude product is filtered and recrystallized from ethanol/water to provide the desired, purified 3-cyano-6-(2-imidazolinylamino)-7-methylindole, hydrobromide salt.

EXAMPLE 13

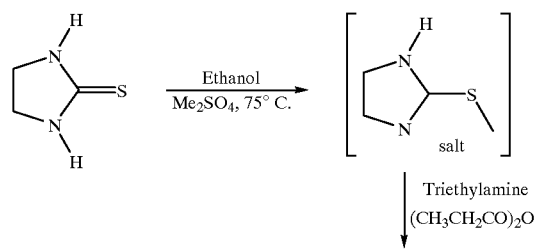

-continued

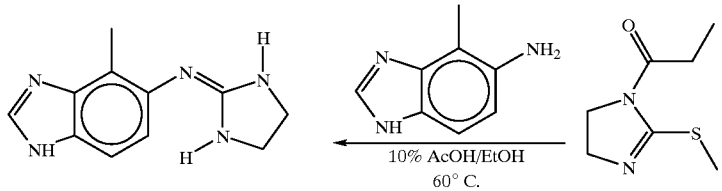

a. 2-Thiomethyl-2-imidazoline

Dimethylsulfate (200 mL) is added to a stirred solution of 2-imidazolidinethione (200 g) in ethanol (2 L). The reaction mixture is heated to 75° C., until the formation of 2-thiomethyl-2-imidazoline is complete.

b. N-Propionyl-2-thiomethyl-2-imidazoline

The mixture in step (a) is cooled to ambient temperature, and to this stirred solution is added triethylamine (1.36 L), followed by propionic anhydride (360 mL). The reaction mixture is stirred until complete, whereupon the mixture is heated to 50° C. The hot solution is filtered to remove the insoluble salts and the salts are washed with cold absolute ethanol. The combined filtrates are cooled to −20° C. and stirred for 2 hours. The solid obtained is filtered, and washed with cold water and then cold absolute ethanol. The product is dried under vacuum at room temperature to provide N-propionyl-2-thiomethyl-2-imidazoline as a solid.

c. 4-Methyl-5-(2-imidazolinylamino)benzimidazole, acetate salt.

N-Propionyl-2-thiomethyl-2-imidazoline (206.4 g) is combined with 5-amino-4-methylbenzimidazole (147 g) (prepared by deprotecting tert-butoxycarbonyl protecting group of intermediate prepared in U.S. Pat. No. 5,478,858 issued to Cupps and Bogdan, Dec. 26, 1995 (incorporated herein by reference), under standard deprotection conditions known in the art) in a 10% solution of acetic acid in ethanol (3 L). The mixture is heated to 60° C. until the reaction is complete. The mixture is then cooled to −20° C. and strirred until the product has completely precipitated. The crude product so obtained is filtered, recrystallized from ethanol/water, and dried (vacuum, ambient temperature) to provide the desired, purified 4-methyl-5-(2-imidazolinylamino)-benzimidazole, acetate salt.

a. 2-Thiomethyl-2-imidazoline

Dimethylsulfate (693 g) is added to a stirred mixture of 2-imidazolidinethione (500 g) in dimethylacetamide (5 L). The reaction mixture is stirred at ambient temperature until the formation of 2-thiomethyl-2-imidazoline is complete.

b. N-Benzoyl-2-thiomethyl-2-imidazoline

The mixture in step (a) is cooled ambient temperature and to this stirred solution is added triethylamine (2.47 kg) followed by benzoyl chloride (964 g). The reaction mixture at ambient temperature until complete. The reaction mixture is added to cold water and the precipitate that forms is filtered and rinsed twice with cold water. The solid obtained is dried (vacuum, ambient temperature) to provide N-benzoyl-2-thiomethyl-2-imidazoline.

c. 7-Methyl-6-(2-imidazolinylamino)indazole hydrochloride

N-Benzoyl-2-thiomethyl-2-imidazoline (264 g) is combined with 6-amino-7-methylindazole (147 g) (as prepared in Example 2 of copending U.S. patent application Ser. No. 60/031,740) in a 10% solution of acetic acid in ethanol (3 L). The mixture is heated to 60° C. until complete. The reaction mixture is cooled to room temperature and hydrogen chloride gas (128 g) is added. The mixture is stirred at ambient temperature for 2 hours, then cooled to −20° C. and stirred until precipitation of the product is complete. The crude product is recrystallized from methyl tert-butyl ether/methanol to provide the desired, purified 7-methyl-6-(2-imidazolinylamino) indazole, hydrochloride salt.

EXAMPLE 14

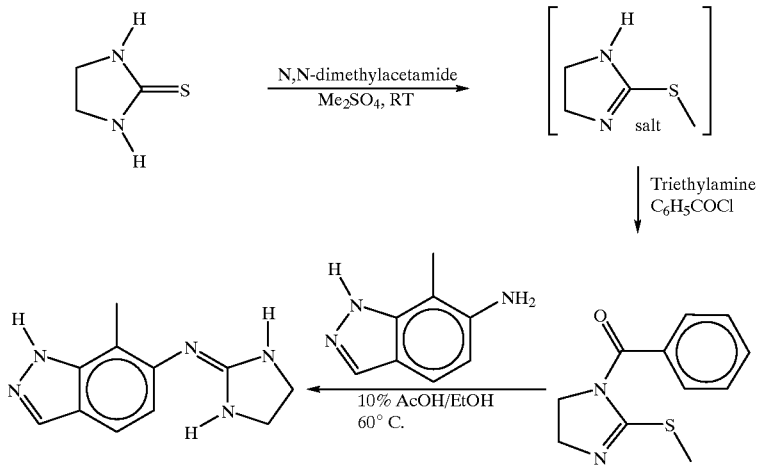

EXAMPLE 15

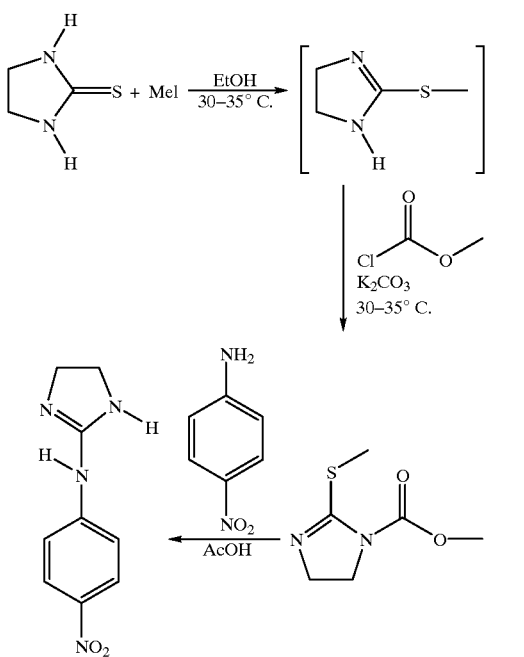

[(4-Nitrophenyl)amino]-2-imidazoline acetate salt

4-Nitroaniline (2 g) and N-methoxycarbonyl-2-thiomethyl-2-imidazoline (3.15 g)(prepared as described in Example 2) are dissolved in glacial acetic acid (40 mL), and the reaction mixture is stirred at 60 to 70° C. until coupling step is complete. The reaction mixture is diluted with methanol (20 mL), refluxed until deprotection is complete, and then concentrated under reduced pressure. The resulting residue is crystallized from ethyl acetate and hexane to furnish [(4-nitrophenyl)amino]-2-imidazoline, mono acetate salt.

EXAMPLE 16

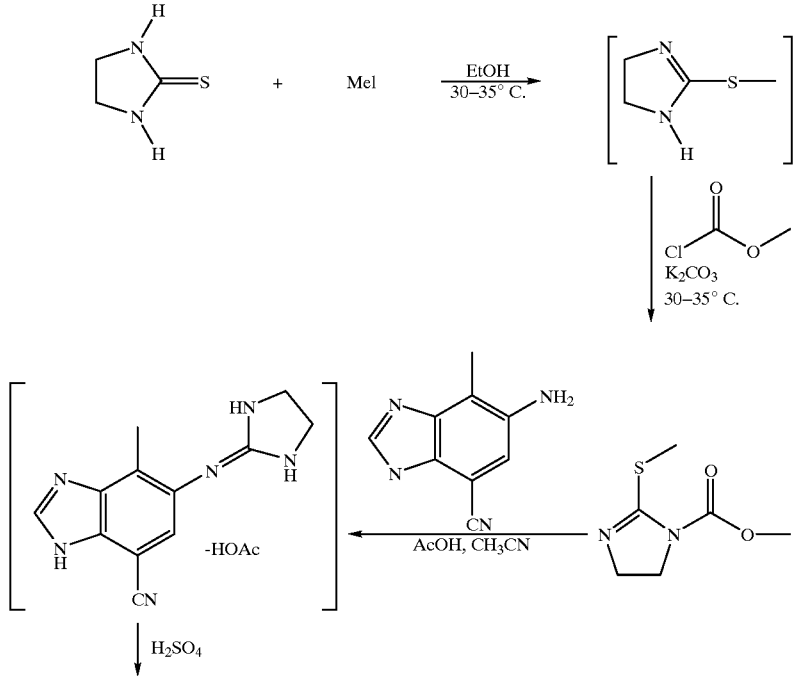

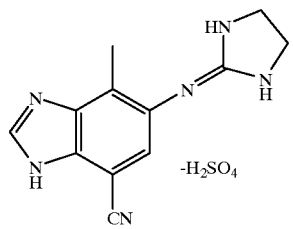

N-(4,5-Dihydro-1H-imidazol-2-yl)-7-cyano-4-methyl-1H-benzimidazol-5-amine, Sulfuric Acid Salt 5-Amino-7-cyano4-methylbenzimidazole (4 g) is prepared treating a heterogeneous solution of 7-cyano-4-methyl-5-nitrobenzimidazole (0.91 g, 0.0045 mol) and 10% Pd/C (100 mg) in methanol (200 mL) with an atmosphere of $H_2$ (1 atm, balloon) for 14 hr. The resulting mixture is filtered through celite and concentrated via rotary evaporation to give rise to a yellow residue. This residue is chromatographed (silica gel, 95:5 ethyl acetate:methanol) to give rise to 5-amino-7-cyano4-methylbenzimidazole. 5-amino-7-cyano-4-methylbenzinidazole N-methoxycarbonyl-2-thiomethyl-2-imidazoline (4.45 g, 1.1 eq.) (prepared as described in Example 2) are dissolved in acetonitrile (100 mL) and glacial acetic acid (10 mL), and the reaction mixture is stirred at 70° C. until the coupling step is complete. The reaction mixture is diluted with methanol (50 mL) and refluxed until deprotection is complete, and then the acetonitrile is evaporated under reduced pressure. The acetic acid solution obtained is dissolved in water (9.25 mL) and the resulting mixture is cooled to 0° C. A 5 molar aqueous solution of $H_2SO_4$ (5.1 mL) is added dropwise to the cold mixture. The solution is then heated to 65° C. and absolute ethanol is added until cloudiness is observed. The mixture is allowed to come to room temperature and is then cooled to 5° C. The solid obtained is filtered, washed with ethanol and dried to provide N-(4,5-dihydro-1H-imidazol-2-yl)-7-cyano-4-methyl-1H-benzimidazol-5-amine as its sulfuric acid salt.

EXAMPLE 17

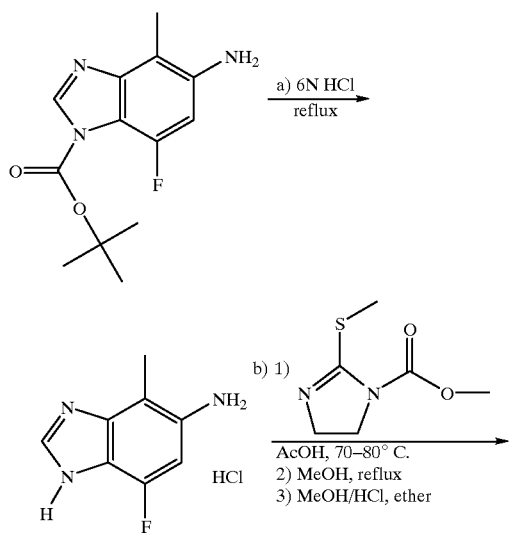

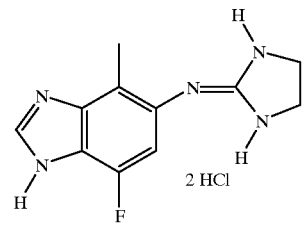

a. 4-Methyl-5-amino-7-fluorobenzimidazole hydrochloride 1-tert-Butoxycarbonyl-4-methyl-5-amino-7-fluorobenzimidazole (1 g) (prepared as described in U.S. Pat. No. 5,478,858 issued to Cupps and Bogdan, Dec. 26, 1995, incorporated herein by reference) and 6N HCl (10 mL) are combined and heated to reflux while stirring. After completion of the t-BOC group deprotection, the reaction mixture is concentrated under reduced pressure and dried to furnish 4methyl-5-amino-7-fluorobenzimidazole hydrochloride.

b. 4-Methyl-7-fluoro-5-(-2-imidazolinylamino) benzimidazole dihydrochloride

To the solid obtained in step a is added N-methoxycarbonyl-2-thiomethyl-2-imidazoline (0.78 g) and glacial acetic acid (20 mL). The mixture is stirred at 60 to 70° C. until the coupling step is complete. The reaction mixture is then diluted with methanol (10 mL), refluxed until deprotection is complete, and then concentrated under reduced pressure. The resulting residue is diluted with methanolic HCl (20 mL) and then treated with anhydrous ether to precipitate 4-methyl-7-fluoro-5-(2-imidazolinylamino)benzimidazole dihydrochloride.

What is claimed is:

1. A method of making a 2-amino-2-imidazoline, guanidine, or 2-amino-3,4,5,6-tetrahydropyrimidine derivative having a general structure:

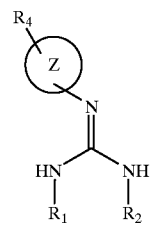

or the tautomers thereof, wherein:

(a) $R_1$ is methyl, ethyl, a methylene group connected to $R_2$ through a single bond such that $R_1$ and $R_2$ form a five-membered ring, or a methylene group connected to $R_2$ through another methylene group such that $R_1$ and $R_2$ form a six-membered ring;

(b) $R_2$ is methyl, ethyl, a methylene group connected to $R_1$ through a single bond such that $R_1$ and $R_2$ form a five-membered ring, or a methylene group connected to $R_1$ through another methylene group such that $R_1$ and $R_2$ form a six-membered ring;

(c) Z is an alkyl or a saturated, unsaturated or aromatic, monocyclic or polycyclic carbocycle or heterocycle containing one or more heteroatoms selected from O, N, or S; and (d) $R_4$ is one or more substituents on Z comprising independently hydrogen, alkoxy, alkylthio, alkyl, alkenyl, amino, carboxyl, cyano, halogen, hydroxy, nitro, and thiol;

(e) or a protected form, salt, pharmaceutically-acceptable salt, biohydrolyzable ester, or solvate thereof;

which comprises the steps of:

(I) preparing an intermediate having the general structure:

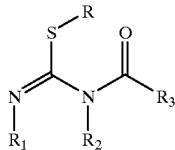

wherein:

(a) R is selected from the group consisting of methyl, ethyl, and benzyl;

(b) $R_1$ is methyl, ethyl, a methylene group connected to $R_2$ through a single bond such that $R_1$ and $R_2$ form a five-membered ring, or a methylene group connected to $R_2$ through another methylene group such that $R_1$ and $R_2$ form a six-membered ring;

(c) $R_2$ is methyl, ethyl, a methylene group connected to $R_1$ through a single bond such that $R_1$ and $R_2$ form a five-membered ring, or a methylene group connected to $R_1$ through another methylene group such that $R_1$ and $R_2$ form a six-membered ring;

(d) $R_3$ is —O—$R_5$ or —$R_6$;

(e) $R_5$ is selected from the group consisting of allyl, methyl, ethyl, benzyl, tert-butyl and phenyl; and (f) $R_6$ is selected from the group consisting of methyl, ethyl, tert-butyl, and phenyl;

from a thiourea having the general structure:

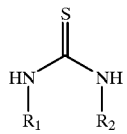

wherein:

(a) $R_1$ is methyl, ethyl, a methylene group connected to $R_2$ through a single bond such that $R_1$ and $R_2$ form a five-membered ring, or a methylene group connected to $R_2$ through another methylene group such that $R_1$ and $R_2$ form a six-membered ring;

(b) $R_2$ is methyl, ethyl, a methylene group connected to $R_1$ through a single bond such that $R_1$ and $R_2$ form a five-membered ring, or a methylene group connected to $R_1$ through another methylene group such that $R_1$ and $R_2$ form a six-membered ring;

in a two-step, one-pot reaction by:

a) alkylating the thiourea using an alkylating agent to form a 2-thio-substituted-2-imidazoline, 2-thioalkyl-2-guanidine, or 2-thioalkyl-2-pyrimidine;

b) acylating the 2-thio-substituted-2-imidazoline, 2-thioalkyl-2-guanidine, or 2-thioalkyl-2-pyrimidine of step (I)(a) with an acylating agent in the presence of a base; and (II) coupling the intermediate of step (I) with an amine or its salts of structure:

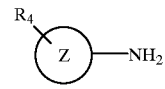

in the presence of an organic acid.

2. A method of making a 2-amino-2-imidazoline, guanidine, or 2-amino-3,4,5,6-tetrahydropyrimidine derivative according to claim 1 wherein the organic acid of step (II) is selected from the group consisting of formic acid, acetic acid, chloroacetic acid, dichloroacetic acid, propionic acid, benzoic acid, maleic acid, fumaric acid, succinic acid, and tartaric acid.

3. A method of making a 2-amino-2-imidazoline, guanidine, or 2-amino-3,4,5,6-tetrahydropyrimidine derivative according to claim 2 wherein the alkylating agent of step (I)(a) is selected from the group consisting of methyl iodide, methyl bromide, methyl chloride, dimethyl sulfate, ethyl iodide, ethyl bromide, ethyl chloride, diethyl sulfate, and benzyl bromide.

4. A method of making a 2-amino-2-imidazoline, guanidine, or 2-amino-3,4,5,6-tetrahydropyrimidine derivative according to claim 3 wherein the base of step (I)(b) is selected from the group consisting of triethylamnine, trimethylamine, 4-dimethylaminopyridine, pyridine, potassium carbonate, sodium carbonate, potassium bicarbonate, and sodium bicarbonate.

5. A method of making a 2-amino-2-imidazoline, guanidine, or 2-amino-3,4,5,6-tetrahydropyrimidine derivative according to claim 4 wherein the acylating agent of step (I)(b) is selected from the group consisting of di-tert-butyl dicarbonate, diethylpyrocarbonate, dimethylpyrocarbonate, methyl chloroformate, ethyl chloroformate, allyl chloroformate, phenyl chloroformate, acetyl chloride, propionyl chloride, acetic anhydride, propionic anhydride, trimethylacetyl chloride, trimethylacetic anhydride, and benzoyl chloride.

6. A method of making a 2-amino-2-imidazoline, guanidine, or 2-amino-3,4,5,6-tetrahydropyrimidine derivative according to claim 5 wherein the alkylation of step I(a) and the acylation of step I(b) are carried out in the presence of an organic solvent selected from the group consisting of methyl tert-butyl ether, ethyl acetate, methanol, ethanol, 2-propanol, and N,N-dimethylacetamide.

7. A method of making a 2-amino-2-imidazoline, guanidine, or 2-amino-3,4,5,6-tetrahydropyrimidine derivative according to claim 6 wherein the coupling of step (II) is carried out in the presence of an organic solvent selected from the group consisting of methanol, ethanol, 2-propanol, butanol, sec-butanol, isoamyl alcohol and acetonitrile.

8. A method of making a 2-amino-2-imidazoline, guanidine, or 2-amino-3,4,5,6-tetrahydropyrimidine derivative according to claim 7 wherein the organic acid of step (II) is selected from the group consisting of acetic acid, propionic acid, and chloroacetic acid.

9. A method of making a 2-amino-2-imidazoline, guanidine, or 2-amino-3,4,5,6-tetrahydropyrimidine derivative according to claim 8 wherein the alkylating agent of step (I)(a) is selected from the group consisting of methyl iodide, methyl bromide, dimethyl sulfate, ethyl iodide, and diethyl sulfate.

10. A method of making a 2-amino-2-imidazoline, guanidine, or 2-amino-3,4,5,6-tetrahydropyrimidine derivative according to claim 9 wherein the base of step (I)(b) is selected from the group consisting of trimethylamine, triethylamine, and potassium carbonate.

11. A method of making a 2-amino-2-imidazoline, guanidine, or 2-amino-3,4,5,6-tetrahydropyrimidine derivative according to claim 10 wherein the acylating agent of step (I)(b) is selected from the group consisting of di-tert-butyl dicarbonate, dimethylpyrocarbonate, and methyl chloroformate.

12. A method of making a 2-amino-2-imidazoline, guanidine, or 2-amino-3,4,5,6-tetrahydropyrimidine derivative according to claim 11 wherein the organic acid of step (II) is acetic acid.

13. A method of making a 2-amino-2-imidazoline, guanidine, or 2-amino-3,4,5,6-tetrahydropyrimidine derivative according to claim 12 wherein the alkylating agent of step (I)(a) is selected from the group consisting of methyl iodide and dimethyl sulfate.

14. A method of making a 2-amino-2-imidazoline, guanidine, or 2-amino-3,4,5,6-tetrahydropyrimidine derivative according to claim 13 wherein the base of step (I)(b) is potassium carbonate.

15. A method of making a 2-amino-2-imidazoline, guanidine, or 2-amino-3,4,5,6-tetrahydropyrimidine derivative according to claim 14 wherein the acylating agent of step (I)(b) is methyl chloroformate.

16. A method of making a 2-amino-2-imidazoline, guanidine, or 2-amino-3,4,5,6-tetrahydropyrimidine derivative according to claim 1 wherein the coupling of step (II) is carried out at a temperature from ambient temperature to about 150° C.

17. A method according to claim 5 wherein the derivative is a 2-amino-2-imidazoline.

18. A method of making a 2-amino-2-imidazoline according to claim 15 wherein the amine of step (II) is 5-amino4-ethylbenzimidazole.

* * * * *

UNITED STATES PATENT AND TRADEMARK OFFICE
CERTIFICATE OF CORRECTION

PATENT NO. : 6,066,740
DATED : May 23, 2000
INVENTOR(S) : Godlewski et al.

It is certified that error appears in the above-identified patent and that said Letters Patent is hereby corrected as shown below:

Title page,
Item [21], insert thereof -- 60/034,318, Nov. 25, 1996 --
Under Inventors, delete "Norwick," and insert thereof -- Norwich, --. The correct form appears in the Declaration dated March 8, 1998.

OTHER PUBLICATIONS,
Line 9, delete "-'-" and insert thereof -- -N'- --. The correct form appears in the IDS submitted on July 1, 1998.

Column 2,
Line 28, delete "New Blocking" and insert thereof -- New Beta Blocking --. The correct form appears in the IDS submitted on July 1, 1998.

ABSTRACT,
Line 3, delete "tetrahydroyrimidine" and insert thereof -- tetrahydropyrimidine --. The correct form appears in the Amendment dated July 27, 1998.
Line 4, delete "subsituted" and insert thereof -- substituted --. The correct form appears in the Amendment dated July 27, 1998.
Line 5, delete "and by further reacting yields", and insert thereof -- in high yields and by further reacting --. The correct form appears in the Amendment dated July 27, 1998.
Line 8, delete "quanidines" and insert thereof -- guanidines --. The correct form appears in the Amendment dated July 27, 1998, Column 1,
Line 31 of the issued patent, delete "intraocular" and insert thereof -- intra-ocular --. The correct form appears in the specification at page 1, lines 28-29.
Line 55 of the issued patent, after "Chemistry" insert -- , --. The correct form appears in the specification at page 2, line 6.
Line 62 of the issued patent, after "Toxicology" insert -- , --. The correct form appears in the specification at page 2, line 10.

Column 14,
Example 2, of the issued patent, delete "30-30° C." and insert thereof -- 30-35° C. --. The correct form appears in the specification at page 18.

UNITED STATES PATENT AND TRADEMARK OFFICE
CERTIFICATE OF CORRECTION

PATENT NO. : 6,066,740
DATED : May 23, 2000
INVENTOR(S) : Godlewski et al.

It is certified that error appears in the above-identified patent and that said Letters Patent is hereby corrected as shown below:

Column 20,
Line 15 of the issued patent, delete "Aminobenizimidazole" and insert thereof -- Aminobenzimidazole --. The correct form appears in the specification at page 23, line 6.

Column 22,
Line 19 of the issued patent, delete ")4methyl-" and insert thereof -- )-4-methyl- --. The correct form appears in the specification at page 24, line 19.

Column 23,
Line 47 of the issued patent, delete "tetratydro" and insert thereof -- tetrahydro --. The correct form appears in the specification at page 26, line 6.

Column 24,
Line 19 of the issued patent, delete "thiomethy14," and insert thereof -- thiomethyl-4 --. The correct form appears in the specification at page 26, line 3.

Column 26,
Line 21 of the issued patent, delete ")4-" and insert thereof -- )-4- --. The correct form appears in the specification at page 28, line 14.

Column 27,
Line 9 of the issued patent, delete "w/v)" and insert thereof -- w/w) --. The correct form appears in the specification at page 29, line 18.

Column 28,
Line 16 of the issued patent, delete 'chioroacetic" and insert thereof -- chloroacetic --. The correct form appears in the specification at page 30, line 22.

UNITED STATES PATENT AND TRADEMARK OFFICE
CERTIFICATE OF CORRECTION

PATENT NO. : 6,066,740
DATED : May 23, 2000
INVENTOR(S) : Godlewski et al.

Page 3 of 3

It is certified that error appears in the above-identified patent and that said Letters Patent is hereby corrected as shown below:

<u>Column 35,</u>
Line 67 of the issued patent, delete "-2-pyrimidine" and insert thereof -- -3,4,5,6-tetrahydropyrimidine --.

Signed and Sealed this

Twenty-seventh Day of November, 2001

Attest:

*Nicholas P. Godici*

NICHOLAS P. GODICI
*Attesting Officer*     *Acting Director of the United States Patent and Trademark Office*